US 8,801,668 B2

(12) United States Patent
Ali et al.

(10) Patent No.: US 8,801,668 B2
(45) Date of Patent: Aug. 12, 2014

(54) DETECTING EMPTY MEDICAL PUMP RESERVOIR

(75) Inventors: Irfan Z. Ali, Woodbury, MN (US); Keith A. Miesel, St. Paul, MN (US); Scott L. Kalpin, Harris, MN (US); Scott A. Sarkinen, Greenfield, MN (US)

(73) Assignee: Medtronic, Inc., Minneapolis, MI (US)

( * ) Notice: Subject to any disclaimer, the term of this patent is extended or adjusted under 35 U.S.C. 154(b) by 0 days.

(21) Appl. No.: 13/553,270

(22) Filed: Jul. 19, 2012

(65) Prior Publication Data
US 2012/0283639 A1 Nov. 8, 2012

Related U.S. Application Data

(63) Continuation of application No. 12/768,336, filed on Apr. 27, 2010, now Pat. No. 8,246,573.

(51) Int. Cl.
*A61M 5/168* (2006.01)
(52) U.S. Cl.
USPC .......................................... 604/151
(58) Field of Classification Search
USPC ............ 604/67, 131, 150–152, 156; 600/587; 417/44.1, 15, 415–420, 505; 73/584
See application file for complete search history.

(56) References Cited

U.S. PATENT DOCUMENTS

| | | | |
|---|---|---|---|
| 3,727,463 A | 4/1973 | Intraub | |
| 4,692,145 A | 9/1987 | Weyant | |
| 4,715,852 A | 12/1987 | Reinicke et al. | |
| 4,985,015 A * | 1/1991 | Obermann et al. | 604/67 |
| 6,555,986 B2 | 4/2003 | Moberg | |
| 6,827,702 B2 | 12/2004 | Lebel et al. | |
| 6,941,785 B2 | 9/2005 | Haynes et al. | |
| 6,945,760 B2 | 9/2005 | Gray et al. | |
| 7,022,116 B2 | 4/2006 | Morris | |
| 7,054,782 B2 | 5/2006 | Hartlaub | |
| 7,099,852 B2 | 8/2006 | Unsworth et al. | |
| 7,290,993 B2 | 11/2007 | Vogeley et al. | |
| 7,367,968 B2 | 5/2008 | Rosenberg et al. | |
| 7,569,030 B2 | 8/2009 | Lebel et al. | |
| 7,581,434 B1 | 9/2009 | Discenzo et al. | |
| 7,621,893 B2 | 11/2009 | Moberg et al. | |
| 7,922,462 B2 | 4/2011 | Preuthun | |
| 8,246,573 B2 | 8/2012 | Ali et al. | |
| 2002/0016568 A1 | 2/2002 | Lebel et al. | |

(Continued)

FOREIGN PATENT DOCUMENTS

AU 525126 B2 10/1982
EP 1338295 A1 8/2003

(Continued)

OTHER PUBLICATIONS

International Search Report and Written Opinion of international application No. PCT/US2011/023115, dated Apr. 26, 2011, 13 pp.

*Primary Examiner* — Quynh-Nhu H Vu
(74) *Attorney, Agent, or Firm* — Shumaker & Sieffert, P.A.

(57) ABSTRACT

A medical device system comprises a reservoir configured to store a therapeutic fluid and a medical pump configured to deliver the therapeutic fluid from the reservoir to a patient. The system also comprises a sensor that can detect a characteristic associated with the pump and a processor to determine if the characteristic detected indicates the reservoir is empty or near empty. The characteristic may comprise a characteristic of a noise made by an actuator within the pump at the end of a pump stroke.

20 Claims, 9 Drawing Sheets

(56) References Cited

U.S. PATENT DOCUMENTS

| | | |
|---|---|---|
| 2002/0058906 A1* | 5/2002 | Lebel et al. .................... 604/65 |
| 2002/0087114 A1 | 7/2002 | Hartlaub |
| 2002/0198513 A1 | 12/2002 | Lebel et al. |
| 2004/0260233 A1 | 12/2004 | Garibotto et al. |
| 2006/0293849 A1 | 12/2006 | Baldwin |
| 2007/0112301 A1 | 5/2007 | Preuthun |
| 2007/0270782 A1 | 11/2007 | Miesel et al. |
| 2008/0132290 A1 | 6/2008 | Sharabi et al. |
| 2008/0294098 A1 | 11/2008 | Sarkinen et al. |
| 2009/0062667 A1* | 3/2009 | Fayram et al. ................ 600/486 |
| 2009/0082757 A1 | 3/2009 | Rogers et al. |
| 2009/0090186 A1* | 4/2009 | Linzenkirchner et al. ...... 73/587 |
| 2009/0099506 A1* | 4/2009 | Estes et al. .................... 604/65 |
| 2012/0109099 A1 | 5/2012 | Rogers et al. |

FOREIGN PATENT DOCUMENTS

| | | |
|---|---|---|
| WO | WO 03023226 A1 | 3/2003 |
| WO | WO 03089034 A1 | 10/2003 |
| WO | WO 2010026570 A2 | 3/2010 |
| WO | WO 2011136862 A1 | 11/2011 |

* cited by examiner

DETECTING EMPTY MEDICAL PUMP RESERVOIR

RELATED APPLICATIONS

This application is a continuation of U.S. patent application Ser. No. 12/768,336, filed Apr. 27, 2010, now allowed, the content of which application is hereby incorporated by reference in its entirety.

TECHNICAL FIELD

The disclosure relates to implantable fluid delivery devices.

BACKGROUND

Implantable fluid delivery devices are used to treat a number of physiological, psychological, and emotional conditions, including chronic pain, tremor, Parkinson's disease, epilepsy, urinary or fecal incontinence, sexual dysfunction, obesity, spasticity, or gastroparesis. For some medical conditions, an implantable fluid delivery device provides the best, and in some cases the only, therapy to restore a patient to a more healthful condition.

An implantable fluid delivery device typically provides a patient with a programmable dosage or infusion of a drug or other therapeutic agent. The fluid delivery device typically includes a reservoir for storing the therapeutic agent, a fill port, a pumping mechanism to pump the therapeutic agent from the reservoir, a catheter port to transport the therapeutic agent from the reservoir to a patient's anatomy, and electronics to control the pumping mechanism.

SUMMARY

In general, the disclosure relates to systems and methods of delivering a therapeutic fluid to a patient from a reservoir and to systems and methods for determining when the reservoir is empty or near empty.

In one embodiment, the disclosure is directed to a medical device system comprising, a reservoir configured to store a therapeutic fluid, a medical pump configured to deliver the therapeutic fluid from the reservoir to a patient, the medical pump comprising an actuation mechanism configured to be energized to provide a pump stroke, a sensor configured to detect a property associated with the energy required to energize the actuation mechanism, and a processor configured to determine when the property associated with the energy required to energize the actuation mechanism indicates the reservoir is empty or near empty.

In another embodiment, the disclosure is directed to a method comprising removing therapeutic fluid from a reservoir using a medical pump comprising an actuation mechanism configured to be energized to provide a pump stroke, detecting a property associated with the energy required to energize the actuation mechanism, and determining that the property associated with the energy required to energize the actuation mechanism indicates the reservoir is empty or near empty.

In another embodiment, the disclosure is directed to a medical device system comprising a reservoir configured to store a therapeutic fluid, a medical pump configured to deliver the therapeutic fluid from the reservoir to a patient, the pump comprising an actuator that is movable through a pump stroke, wherein the actuator makes a noise at an end of the pump stroke, a sensor configured to detect a characteristic of the noise, and a processor configured to determine when the characteristic of the noise indicates the reservoir is empty or near empty.

In another embodiment, the disclosure is directed to a method comprising removing therapeutic fluid from a reservoir using a medical pump comprising an actuator that is movable through a pump stroke, wherein the actuator makes a noise at an end of the pump stroke, detecting a characteristic of the noise, and determining that the characteristic of the noise indicates the reservoir is empty or near empty.

The details of one or more embodiments of the disclosure are set forth in the accompanying drawings and the description below. Other features, objects, and advantages of the disclosure will be apparent from the description and drawings, and from the claims.

DETAILED DESCRIPTION

An implantable fluid delivery device may include a reservoir for storing a fluid, such as a drug or other therapeutic agent, for delivery to the patient. The implantable fluid delivery device may also include a pump, such as an electromagnetic piston pump, for delivering the therapeutic agent from the reservoir to the patient. The amount of fluid in the reservoir is typically known when the reservoir is first filled with the therapeutic agent.

Additionally, the fluid delivery device may be configured to determine how much of the therapeutic remains in the reservoir based on the amount of the therapeutic agent that has been delivered to the patient. However, in some cases, either the initial amount of the therapeutic agent loaded into the reservoir or the amount of fluid that has been delivered by the pump can be incorrect. For example, occasionally a clinician may accidentally inject some of the therapeutic agent that was intended to be loaded into the reservoir into the subcutaneous pocket in which the fluid delivery device has been implanted, also known as a "pocket fill."

In general, this disclosure is directed to techniques for providing a medical device for the delivery of a therapeutic fluid with empty-reservoir detection so that the fluid delivery device will become aware that the reservoir is empty or near empty. In one example, the medical device may include a reservoir configured to store a therapeutic fluid and a medical pump configured to deliver the therapeutic fluid from the reservoir to a patient. The pump may include an actuation mechanism configured to be energized to provide a pump stroke, such as an electromagnetic coil and an actuator that is movable in response to the coil being energized. The device also may include a sensor configured to detect a property associated with the energization of the actuation mechanism that indicates the reservoir is empty or near empty. The device may also include a processor configured to determine when the property associated with the energization of the actuation mechanism indicates the reservoir is empty or near empty. In another example, the device may include a reservoir, a pump configured to deliver a therapeutic fluid from the reservoir to a patient, wherein the pump comprises an actuator that is movable through a pump stroke. The actuator may make a noise at the end of a pump stroke. The fluid delivery device may include a sensor that detects a characteristic of the noise and a processor configured to determine when the characteristic of the noise indicates the reservoir is empty or near empty. The medical device may be fully implantable, or may comprise components that are external and a catheter or other means to deliver the fluid from the external components to the patient, such as a percutaneous port.

Figure 1:
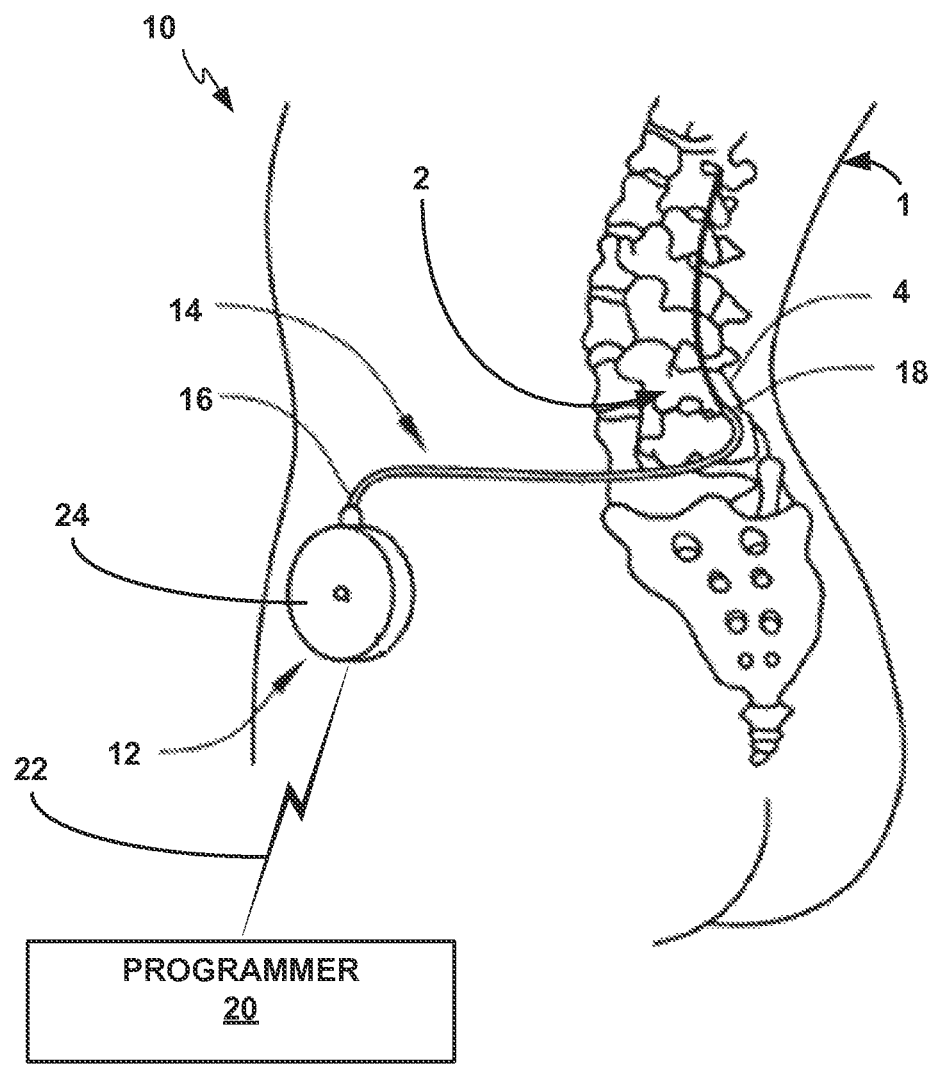
FIG. 1 is a conceptual diagram illustrating an example of a fluid delivery system, which includes an implantable fluid delivery device with a medical pump that is configured to deliver a therapeutic agent to a patient via a catheter.

FIG. 1 is a schematic diagram of an example system 10, including an implantable medical device (IMD) 12, which is configured to deliver a therapeutic agent, such as a pharmaceutical agent, for example a drug, insulin, pain relieving agent, anti-inflammatory agent, gene therapy agent, or the like, to a target site 2 within a patient 1. The therapeutic agent is delivered via a catheter 14 that is coupled to IMD 12. Catheter 14 may comprise a plurality of catheter segments, or catheter 14 may be a unitary catheter. In the example shown in FIG. 1, target site 2 is proximate to spinal cord 4 of patient 1.

A proximal end 16 of catheter 14 is coupled to IMD 12 while a distal end 18 of catheter 14 is positioned proximate target site 2. System 10 May also include an external programmer 20 that communicates with IMD 12 as needed, such as to provide or retrieve therapy information or other treatment parameters associated with therapy delivery. For example, external programmer 20 may be configured to turn IMD 12 on or off, to deliver the initial therapy parameters for patient 1, to modify the therapy parameters, and so forth. In one example, external programmer 20 communicates with IMD 12 wirelessly 22, as shown in FIG. 1.

Although patient 1 is generally referred to as a human patient in the present disclosure, system 10 can be used with other mammalian or non-mammalian patients. IMD 12 may be employed to treat, manage or otherwise control various conditions or disorders of patient 1, including, e.g., pain (e.g., chronic pain, post-operative pain or peripheral and localized pain), tremor, movement disorders (e.g., Parkinson's disease), diabetes, epilepsy, neuralgia, chronic migraines, urinary or fecal incontinence, sexual dysfunction, obesity, gastroparesis, mood disorders, or other disorders.

IMD 12 may be configured to deliver one or more therapeutic agents, alone or in combination with other therapies, including, e.g., electrical stimulation. For example, in some cases, a medical pump may deliver one or more pain-relieving drugs to patients with chronic pain, insulin to a patient with diabetes, or other fluids to patients with different disorders. IMD 12 may be implanted in patient 1 for chronic or temporary therapy delivery.

IMD 12 includes an outer housing 24 that is constructed of a biocompatible material that resists corrosion and degradation from bodily fluids, such as titanium or biologically inert polymers. IMD 12 may be implanted within a subcutaneous pocket close to target site 2. For example, as shown in FIG. 1, IMD 12 may be implanted within the abdomen of patient 1 close to the position along spinal cord 4 where target site 2 is located. In other examples, IMD 12 may be implanted within other suitable sites within patient 1, which may depend, for example, on where target site 2 is located within patient 1, and the ease of implanting IMD 12 within suitable locations near target site 2.

Catheter 14 may be coupled to IMD 12 either directly or with the aid of a catheter extension (not shown). In the example shown in FIG. 1, catheter 14 traverses from the implant site of IMD 12 to target site 2 proximate to spinal cord 4. Catheter 14 is positioned such that one or more fluid delivery outlets of catheter 14 are proximate to one or more locations within patient 1. In the example shown in FIG. 1, IMD 12 delivers a therapeutic agent to one or more locations at target site 2 within patient 1. IMD 12 delivers a therapeutic agent to target site 2 proximate spinal cord 4 with the aid of catheter 14. For example, IMD 12 may be configured for intrathecal drug delivery into the intrathecal space or epidural space surrounding spinal cord 4.

In some examples, multiple catheters may be coupled to IMD 12 to target the same or different tissue or nerve sites within patient 1. Thus, although a single catheter 14 is shown in FIG. 1, in other examples, system 10 may include multiple catheters or catheter 14 may define multiple lumens for delivering different therapeutic agents to patient 1 or for delivering a therapeutic agent to different tissue sites within patient 1. Accordingly, in some examples, IMD 12 may include a plurality of reservoirs for storing more than one type of therapeutic agent. In some examples, IMD 12 may include a single long tube that contains the therapeutic agent in place of a reservoir. However, for ease of description, an IMD 12 including a single reservoir is primarily discussed herein with reference to the example of FIG. 1.

IMD 12 may deliver one or more therapeutic agents to patient 1 according to one or more therapy programs. Example therapeutic agents that IMD 12 may be configured to deliver include insulin, morphine, hydromorphone, bupivacaine, clonidine, other analgesics, genetic agents, antibiotics, nutritional fluids, analgesics, hormones or hormonal drugs, gene therapy drugs, anticoagulants, cardiovascular medications or chemotherapeutics. A therapy program, generally speaking, may set forth different therapy parameters, such as a therapy schedule specifying programmed doses, dose rates for the programmed doses, and specific times to deliver the programmed doses.

The therapy programs may be a part of a program group for therapy, wherein the group includes a plurality of constituent therapy programs and/or therapy schedules. In some examples, IMD 12 may be configured to deliver a therapeutic agent to patient 1 according to different therapy programs on a selective basis. IMD 12 may include a memory to store one or more therapy programs, instructions defining the extent to which patient 1 may adjust therapy parameters, switch between therapy programs, or undertake other therapy adjustments. Patient 1 may select and/or generate additional therapy programs for use by IMD 12 via external programmer 20 at any time during therapy or as designated by the clinician.

Programmer 20 is an external computing device that is configured to wirelessly communicate with IMD 12. For example, programmer 20 may be a clinician programmer that the clinician uses to communicate with IMD 12. Alternatively, programmer 20 may be a patient programmer that allows patient 1 to view and modify therapy parameters. A clinician programmer may include additional or alternative programming features, relative to a patient programmer. For example, more complex or sensitive tasks may only be allowed by the clinician programmer to prevent patient 1 from making undesired changes to the operation of IMD 12.

Programmer 20 may be a hand-held computing device that includes a display viewable by the user and a user input mechanism that can be used to provide input to programmer 20. For example, programmer 20 may include a display screen (e.g., a liquid crystal display or a light emitting diode display) that presents information to the user. In addition, programmer 20 may include a keypad, buttons, a peripheral pointing device, touch screen, voice recognition, or another input mechanism that allows the user to navigate though the user interface of programmer 20 and provide input.

In other examples, rather than being a handheld computing device or a dedicated computing device, programmer 20 may be a larger workstation or a separate application within another multi-function device. For example, the multi-function device may be a cellular phone, personal computer, laptop, workstation computer, or personal digital assistant that can be configured to an application to simulate programmer 20. Alternatively, a notebook computer, tablet computer, or other personal computer may execute an application to function as programmer 20, e.g., with a wireless adapter connected to the personal computer for communicating with IMD 12.

When programmer 20 is configured for use by the clinician, programmer 20 may be used to transmit initial programming information to IMD 12. This initial information may include hardware information for system 10 such as the type of catheter 14, the position of catheter 14 within patient 1, the type of therapeutic agent(s) delivered by IMD 12, a baseline orientation of at least a portion of IMD 12 relative to a reference point, therapy parameters of therapy programs stored within IMD 12 or within programmer 20, and any other information the clinician desires to program into IMD 12.

A clinician uses programmer 20 to program IMD 12 with one or more therapy programs that define the therapy delivered by IMD 12. During a programming session, the clinician may determine one or more therapy programs, which may include one or more therapy schedules, programmed doses, dose rates of the programmed doses, and specific times to deliver the programmed doses that may provide effective therapy to patient 1. Patient 1 may provide feedback to the clinician as to the efficacy of a specific therapy program being evaluated or desired modifications to the therapy program. Once the clinician has identified one or more programs that may be beneficial to patient 1, patient 1 may continue the evaluation process and determine which dosing program or therapy schedule best alleviates the condition of patient 16 or otherwise provides efficacious therapy to patient 1.

In some cases, programmer 20 may be configured for use by patient 1. When configured as the patient programmer, programmer 20 may have limited functionality in order to prevent patient 1 from altering critical functions or applications that may be detrimental to patient 1. In this manner, programmer 20 may only allow patient 1 to adjust certain therapy parameters or set an available range for a particular therapy parameter. In some cases, a patient programmer may permit the patient to control IMD 12 to deliver a supplemental, patient bolus, if permitted by the applicable therapy program administered by the IMD, e.g., if delivery of a patient bolus would not violate a lockout interval or maximum dosage limit. Programmer 20 may also provide an indication to patient 1 when therapy is being delivered or when IMD 12 needs to be refilled or when the power source within programmer 20 or IMD 12 needs to be replaced or recharged.

Whether programmer 20 is configured for clinician or patient use, programmer 20 may communicate to IMD 12 or any other computing device via wireless communication. Programmer 20, for example, may communicate via wireless communication link 22 with IMD 12 using any of a number of radio frequency (RF) telemetry techniques. Programmer 20 may also communicate with another programmer or computing device via a wired or wireless connection using any of a variety of local wireless communication techniques, such as RF communication according to one or more specification sets, such as the Medical Implant Communication Service (MICS) specification set, Medical Implant Telemetry System (MITS), Medical Data Service (MEDS), 802.11, or Bluetooth specification sets, infrared (IR) communication according to the IRDA specification set, or other standard or proprietary telemetry protocols. Programmer 20 may also communicate with another programmer or computing device via exchange of removable media, such as magnetic or optical disks, or memory cards or sticks. Further, programmer 20 may communicate with IMD 12 and another programmer via remote telemetry techniques, communicating via a local area network (LAN), wide area network (WAN), public switched telephone network (PSTN), or cellular telephone network, for example.

Figure 2:
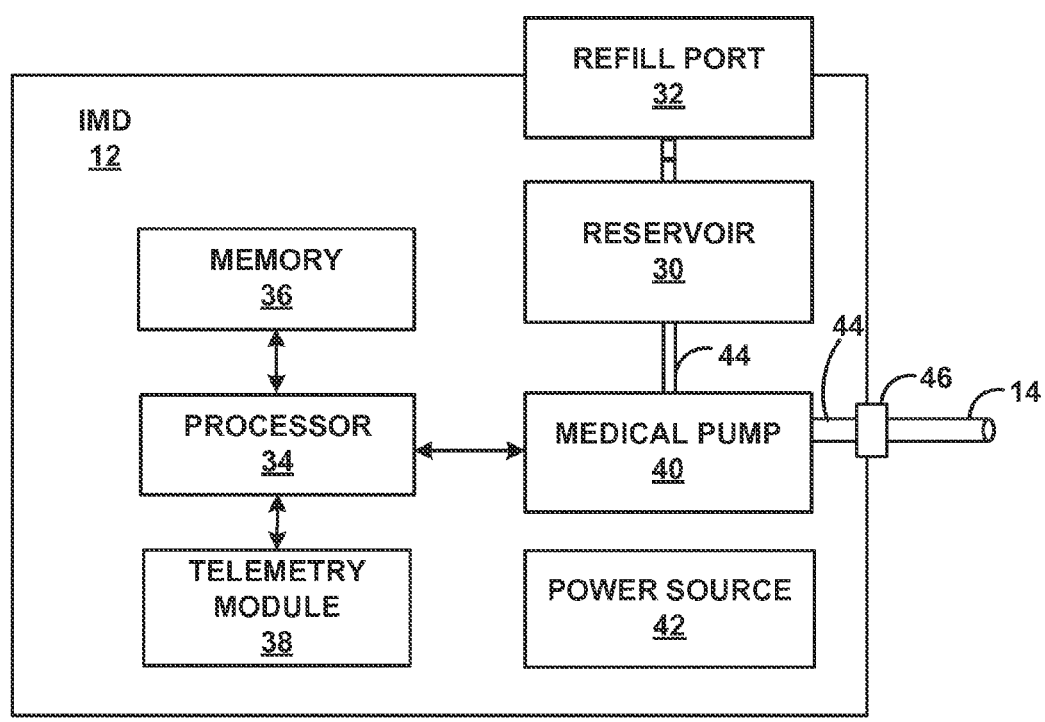
FIG. 2 is functional block diagram illustrating an example fluid delivery device with a medical pump.

FIG. 2 is a functional block diagram illustrating components of an example of IMD 12. The example IMD 12 shown in FIG. 2 includes reservoir 30, refill port 32, processor 34, memory 36, telemetry module 38, medical pump 40, power source 42, internal channels 44, and catheter access port 46.

Refill port 32 may comprise a self-sealing injection port. The self-sealing injection port may include a self-sealing membrane to prevent loss of therapeutic agent delivered to reservoir 30 via refill port 32. After a delivery system, e.g., a hypodermic needle, penetrates the membrane of refill port 32, the membrane may seal shut when the delivery system is removed from refill port 32. Internal channels 44 comprises one or more segments of tubing or a series of cavities that run from reservoir 30, around or through medical pump 40 to catheter access port 46.

Processor 34 controls the operation of medical pump 40 with the aid of software instructions associated with program information that is stored in memory 36. In one example, processor 34 is configured to run the software instructions in order to control operation of IMD 12. For example, the software instructions may define therapy programs that specify the amount of a therapeutic agent that is delivered to a target tissue site within patient 1 from reservoir 30 via catheter 14, e.g., dose, the rate at which the agent is delivered, e.g., dosage rate, and the time at which the agent will be delivered and the time interval over which the agent will be delivered, e.g., the therapy schedule for dose or doses defined by program. In other examples, a quantity of the therapeutic agent may be delivered according to one or more physiological characteristics of a patient, e.g., physiological characteristics sensed by one or more sensors (not shown) implanted within a patient as part of therapy system 10 (FIG. 1). Processor 34 can include one or more processors, including one or more microprocessors, digital signal processors (DSPs), application specific integrated circuits (ASICs), field programmable gate arrays (FPGAs), or any other equivalent integrated or discrete logic circuitry, as well as any suitable combination of such components. The term "processor" or "processing circuitry" may generally refer to any of the foregoing logic circuitry, alone or in combination with other logic circuitry, or any other equivalent circuitry.

Memory 36 may include any volatile or non-volatile media, such as a random access memory (RAM), read only memory (ROM), non-volatile RAM (NVRAM), electrically erasable programmable ROM (EEPROM), flash memory, and the like. As mentioned above, memory 36 may store program information including instructions for execution by processor 34, such as, but not limited to, therapy programs, historical therapy programs, timing programs for delivery of the therapeutic agent from reservoir 30 to catheter 14, and any other information regarding therapy of patient 1. Memory 36 may include separate memory portions for storing instructions, patient information, therapy parameters (e.g., grouped into sets referred to as "dosing programs"), therapy adjustment information, program histories, and other categories of information such as any other data that may benefit from separate physical memory modules.

Telemetry module 38 in IMD 12, as well as telemetry modules in programmers, such as external programmer 20, may accomplish communication by RF communication techniques. In addition, telemetry module 38 may communicate with programmer 20 via proximal inductive interaction of IMD 12 with external programmer 20. Processor 34 controls telemetry module 38 to send and receive information.

Power source 42 delivers operating power to various components of IMD 12. Power source 42 may include a small rechargeable or non-rechargeable battery and a power generation circuit to produce the operating power. In the case of a rechargeable battery, recharging may be accomplished through proximal inductive interaction between an external charger and an inductive charging coil within IMD 12. In some examples, power requirements may be small enough to allow IMD 12 to utilize patient motion and implement a kinetic energy-scavenging device to trickle charge a rechargeable battery. In other examples, traditional batteries may be used for a limited period of time. As a further alternative, an external inductive power supply could transcutaneously power IMD 12 whenever measurements are needed or desired.

Figure 3:
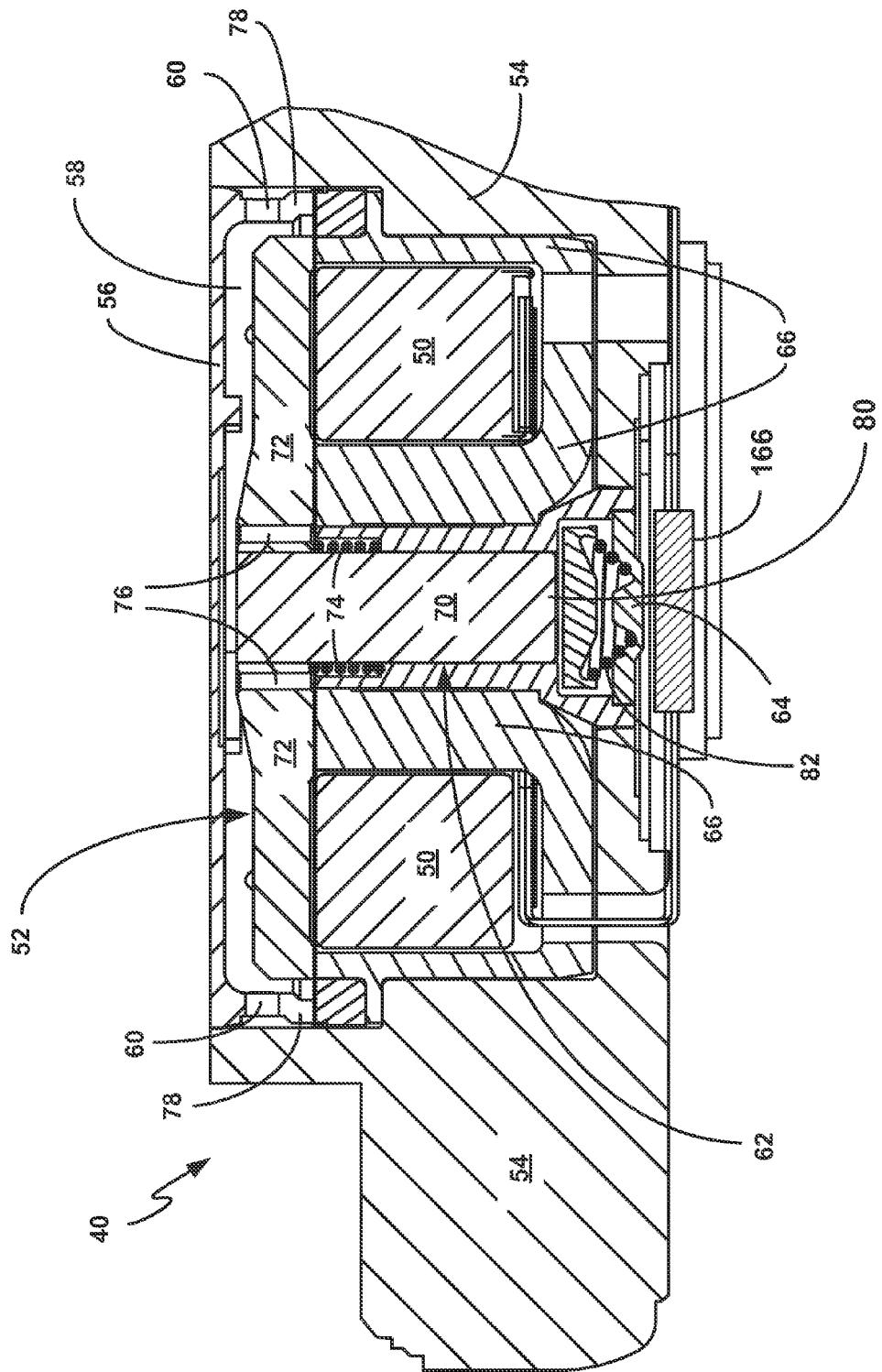
FIG. 3 is a broken section view of an example medical pump for use in the fluid delivery device of FIG. 1.

Medical pump 40 may be a mechanism that delivers a therapeutic agent in some metered or other desired flow dosage to target site 2 within patient 1 from reservoir 30 via catheter 14. Medical pump 40 may include an actuation mechanism that is electrically energized to provide a pump stroke to move fluid from reservoir 30. The actuation mechanism may comprise an electromagnetic coil and an actuator that is movable in response to electrical energization of the coil. Other actuation mechanisms may be used, such as a piezoactuator. FIG. 3 is a broken section view of an example of medical pump 40 including electromagnetic coil 50, actuator 52, bulkhead 54, and cover 56. During the operation of medical pump 40, the therapeutic agent flows from reservoir 30 into chamber 58 formed within bulkhead 54. In one example, the therapeutic agent enters chamber 58 through holes 60 in cover 56. Once within chamber 58, the therapeutic agent enters central aperture 62 and is pushed by the motion of actuator 52 through one-way valve 64. After passing through one-way valve 64, the therapeutic agent is directed through internal channels 44 to catheter 14 and onto to one or more target sites within the patient. For example, as shown in FIG. 1, catheter 14 may be used to direct the therapeutic agent from medical pump 40 to target site 2 within patient 1.

Electromagnetic coil 50 comprises one or more insulated conductors arranged in a multitude of turns. As examples, electromagnetic coil 50 may include a single continuous conductor or more than one conductor electrically connected in series or in parallel. Current is delivered to electromagnetic coil 50 to produce a magnetic field that moves actuator 52 through a pump stroke from a rearward position (upward in FIG. 3) to a forward position (downward in FIG. 3). In one example, electromagnetic coil 50 is retained in a magnetic cup 66 that includes a highly magnetic material that efficiently magnetizes in response to current through electromagnetic coil 50. As an example, magnetic cup 66 may include a highly magnetic steel alloy, such as a highly magnetic stainless steel alloy, for example 430F stainless steel.

In the example shown in FIG. 3, actuator 52 includes a piston 70 and an armature 72. Actuator 52 is positioned such that piston 70 is located within central aperture 62. A spring 74 is located within central aperture 62 adjacent armature 72. Spring 74 biases actuator 52 into a rearward position away from coil 50 (upward as shown in FIG. 3). Armature 72 is made from a magnetic material, such as a stainless steel. When coil 50 and magnetic cup 66 are magnetized, armature 72 is attracted to and moves toward magnetic cup 66 so that actuator 52 moves to a forward position (downward as shown in FIG. 3), producing a pump stroke. The therapeutic agent flows into chamber 58 where it is forced out of medical pump 40 by the motion of actuator 52. In one example, the therapeutic agent flows through holes 60 formed in cover 56 into chamber 58, through holes 76 in armature 72 and/or around armature 72 through a gap between armature 72 and a sidewall 78 of cover 56 and into central aperture 62, where the therapeutic agent is forced out one-way valve 64 by piston 70 when actuator 52 is driven from the rearward position to the forward position. Because armature 72 is within the therapeutic agent flow path, the material of armature 72 should resist corrosion, such as a magnetic stainless steel alloy that is corrosion resistant, such as AL29-4 stainless steel.

Piston 70 may be interference fit to armature 72 or secured to armature 72 by other suitable techniques. Like armature 72, piston 70 is located within the therapeutic agent flow path and should resist corrosion. In one example, piston 70 comprise a sapphire material, which resists corrosion and limits wear between piston 70 and central aperture 62 caused by the pumping action of medical pump 40. Piston 70 may comprise other materials, however, such as a metal material, for example a stainless steel or titanium alloy. In some examples, actuator 52 may comprise a unitary component wherein piston 70 and armature 72 comprise a single magnetic material such as a stainless steel alloy.

Actuator 52 actuates so that armature 72 moves within chamber 58 between the rearward position and the forward position. Spring 74 biases actuator 52 toward the rearward position with armature 72 being pushed against an interior surface of cover 56. Energizing electromagnetic coil 50 magnetizes magnetic cup 66, which in turn attracts armature 72. The magnetic attraction force between armature 72 and magnetic cup 66 overcomes the force of spring 74 to move actuator 52 through a pump stroke from the rearward position to forward position (downward in FIG. 3) to create a pumping action of piston 70. The motion of piston 70 forces the therapeutic agent within central aperture 62 and adjacent to a distal end 80 of piston 70 through one-way valve 64.

Following a pump stroke, current through electromagnetic coil 50 is stopped, and spring 74 biases actuator 52 into its original rearward position with armature 72 pushed against cover 56. As spring 74 moves actuator 52 into the rearward position, the therapeutic agent flows through a small gap between piston 70 and central aperture 62 to fill the growing space within central aperture 62 between distal end 80 of piston 70 and one-way valve 64. While some of the therapeutic agent may flow back though the gap between piston 70 and central aperture 62 during a pump stroke, the speed of piston 70 during a pump stroke combined with the viscosity of the therapeutic agent generally makes any amount of the therapeutic agent flowing back though the gap between piston 70 and the inner surface of central aperture 62 during a pump stroke negligible.

The therapeutic agent pushed by piston 70 during a pump stroke exits medical pump 40 through one-way valve 64. In one example, one-way valve 64 includes a spring 82 that biases one-way valve 64 into a closed position when actuator 52 is not being driven forward. When actuator 52 is driven from the rearward position to the forward position, as described above, the force of the therapeutic agent being pushed forward counteracts the force of spring 82 and opens one-way valve 64 so that the therapeutic agent can flow through one-way valve 64. The configuration of one-way valve 64 may be referred to as a lift check valve. In other examples, different valve configurations may be used including, but not limited to, ball check valves, diaphragm valves, gate valves and other valves. Generally, one-way valve 64 should be selected to minimize a pressure differential in the therapeutic agent flow path at one-way valve 64 while maintaining a fluid seal except during pump strokes.

Further examples of medical pumps that may be used in IMD 12 are disclosed in U.S. Provisional Patent Application Ser. No. 61/174,457, filed on Apr. 30, 2009, the disclosure of which is incorporated herein by reference in its entirety.

Figure 4:
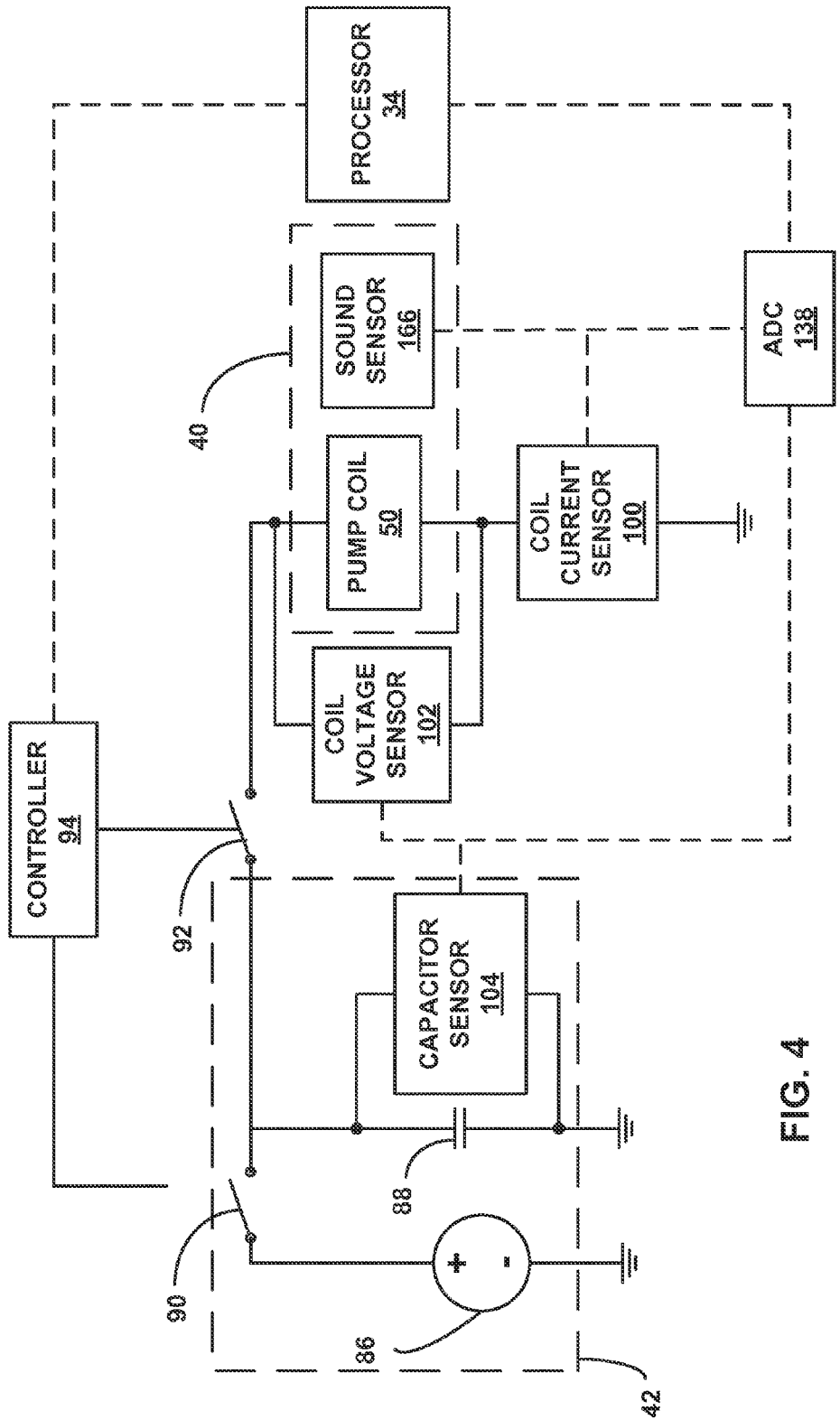
FIG. 4 is a block diagram showing an example circuit for energizing the medical pump and detecting an empty reservoir.

FIG. 4 is a block diagram of an example circuit for energizing coil 50 and for detecting when reservoir 30 is empty. As shown in the example of FIG. 4, power source 42 is electrically connected to medical pump 40. Power source 42 may include a small rechargeable or non-rechargeable battery 86 and a capacitor 88. Although a single capacitor 88 is shown in FIG. 4, power source 42 may comprise a plurality of capacitors connected together, wherein the plurality of capacitors are equivalent to the single capacitor 88 shown in FIG. 4. Battery 86 is operatively connected to capacitor 88 via a first switching device 90 to provide for selective charging of capacitor 88 using battery 86. In one example, capacitor 88 is also operatively connected to coil 50 of medical pump 40 via a second switching device 92 in order to selectively discharge energy to coil 50. One or more controllers 94 may be provided to control switching devices 90, 92 for controlling the flow of electrical energy from power source 42 to medical pump 40. Controller 94 receives instructions from processor 34 regarding when medical pump 40 should deliver a pump stroke.

Use of capacitor 88 provides for a generally fast-response power pulse to coil 50 on command and provides for a reliable constant initial voltage and current across coil 50. When capacitor 88 is charged and processor 34 instructs controller 94 to initiate a pump stroke, controller 94 closes switching device 92 to electrically couple capacitor 88 to coil 50, allowing capacitor 88 to energize coil 50. When coil 50 is energized, a magnetic field is created that drives actuator 52 through a pump stroke, as described above.

Switching device 92 may be opened by controller 94 after a predetermined period of time or after the detection of an end of the pump stroke. Examples of methods of detecting the end of the pump stroke and methods of controlling the pump using end-of-stroke detection is disclosed in pending U.S. patent application Ser. No. 11/805,124, corresponding to U.S. Published Application No. US 2008/0294098, the disclosure of which is incorporated herein by reference in its entirety. Upon the opening of switching device 92, capacitor 88 is electrically decoupled from coil 50, and electrical energy in coil 50 dissipates such that the mechanical force applied by spring 74 (FIG. 3) returns actuator 52 to its rearward position.

After capacitor 88 has been discharged through coil 50 and switching device 92 has been opened, capacitor 88 may be recharged when controller 94 closes switching device 90 between battery 86 and capacitor 88 to electrically couple battery 86 to capacitor 88 in order to recharge capacitor 88 for subsequent pump stroke operation. In this way, capacitor 88 is controlled to charge and discharge to provide the electrical energy to coil 50 as needed to affect a plurality of pump strokes of actuator 52.

It will be recognized by a person of ordinary skill in the art that any suitable switching device capable of providing the switching connections described above may be used for switching device 90 between battery 86 and capacitor 88 and for switching device 92 between capacitor 88 and coil 50 of medical pump 40. For example, switching devices 90, 92 may each be a field-effect transistor (FET) or a junction transistor that is controlled, for example, by controller 94, to close and/or open when commanded. Other suitable electronic or electromagnetic switch configurations, junction transistors, relays, or the like, may be employed as switching devices 90, 92.

Continuing with the block diagram of FIG. 4, IMD 12 may include one or more sensors for detecting a property associated with the energy required to energize coil 50 and drive actuator 52 so that the sensor may be configured to detect whether a particular pump stroke indicates reservoir 30 is empty. In one example, IMD 12 includes a current sensor 100 for determining the current passing through coil 50 and/or a voltage sensor 102 for determining the voltage across coil 50. IMD 12 may also include a voltage sensor 104 for determining the voltage across capacitor 88.

Figure 5:
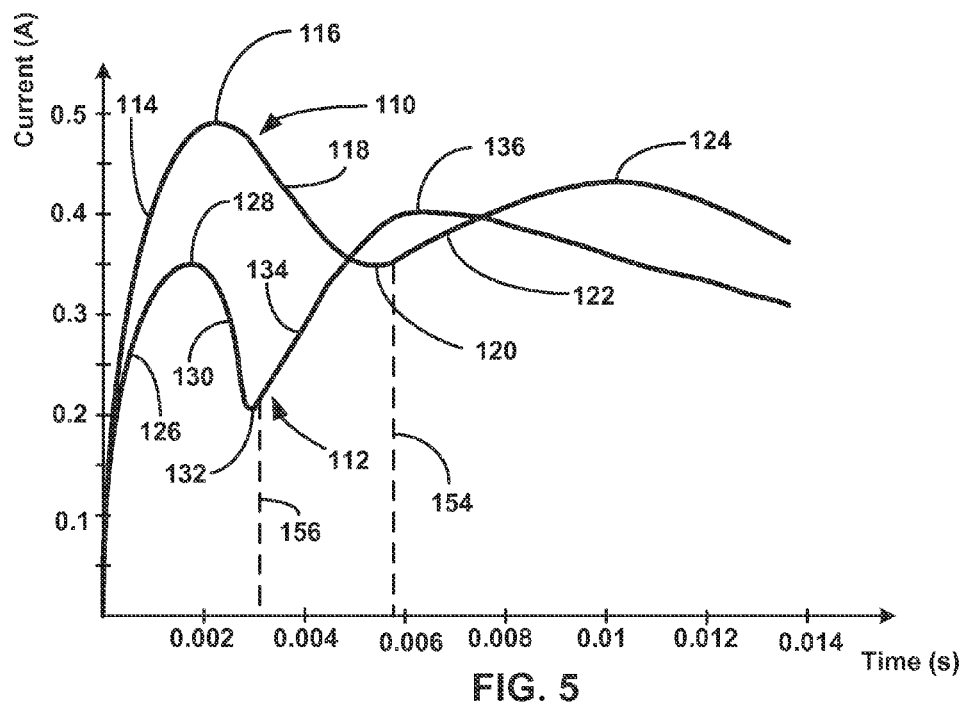
FIG. 5 is graph showing example current waveforms through a coil of the medical pump for a pump stroke from a reservoir containing therapeutic agent and a pump stroke from an empty reservoir.

Coil current sensor 100 allows the current waveform of coil 50 to be determined during a pump stroke. Example current waveforms for coil 50 are shown in FIG. 5. FIG. 5 shows an example waveform 110 for medical pump 40 wherein reservoir 30 contains some of the therapeutic agent. A pump stroke that occurs when reservoir 30 contains some of the therapeutic agent, e.g., that produces a current waveform similar to waveform 110 shown in FIG. 5, is referred to herein as a "normal" pump stroke of medical pump 40. Normal pump strokes generally occur when reservoir 30 is between about 5 percent and 100 percent full. In one example, wherein reservoir 30 has a capacity of about 20 mL, a normal pump stroke waveform is expected when there is at least about 1 mL of therapeutic agent remaining in reservoir 30. In another example, wherein reservoir 30 has a capacity of about 40 mL, a normal pump stroke waveform is expected when there is at least about 2 mL of therapeutic agent remaining in reservoir 30.

As shown in FIG. 5, at time=0, switching device 92 has been closed and current begins to flow from capacitor 88 through coil 50. For an initial segment 114, the current through coil 50 rising quickly up to a maximum current peak 116. At peak 116, actuator 52 begins to move, and as actuator 52 moves it creates a back electromotive force (EMF) effect that counters the current caused by capacitor 88 such that during a segment 118 the current begins to decline. The back EMF effect continues to cause a decrease in current throughout segment 118 until trough 120 when actuator 52 completes a pump stroke and stops moving so that the back EMF effect is no longer being produced. Without the back EMF effect, the current through coil 50 rebounds at segment 122. Throughout this entire time, however, capacitor 88 is depleting its charge such that the voltage provided by capacitor 88, and hence the current it can provide to coil 50, decays. This decaying of current eventually overtakes the rebound effect in segment 122, and at peak 124 the current begins to decline until capacitor 88 is completely depleted of charge. The actual values of peak 116, trough 120, and final peak 124, as well as the slopes of segments 114, 118, 122, and the segment after final peak 124 may depend on the specific fluid being delivered.

FIG. 5 also shows an example current waveform 112 for a pump stroke when reservoir 30 is empty. Like the normal pump stroke waveform 110, waveform 112 includes an initial segment 126 where the current increases quickly to an initial peak 128, followed by a segment 130 of decreasing current until a trough 132 is reached, followed by a rebound segment 134, and a final peak 136. As with normal waveform 110, initial peak 128 indicates the point when actuator 52 begins to move and trough 132 indicates the point when actuator 52 has completed a pump stroke. For example, characteristics of the therapeutic agent being delivered, such as the molecular weight of a drug being delivered or a viscosity of the therapeutic agent fluid, may affect the current waveform shape. Another factor that may affect the current waveform shape is the battery depletion over the life of IMD 12.

As is apparent by a comparison of normal waveform 110 and empty-reservoir waveform 112, it requires more energy to drive actuator 52 through a normal pump stroke because there must be sufficient energy to not only move actuator 52, but also to move the therapeutic agent out of pump 40 through one-way valve 64. Conversely, it requires less energy to move actuator 52 through a pump stroke when reservoir 30 is empty because actuator 52 does not have to move any therapeutic agent when reservoir 30 is empty. The difference in energy required to move actuator 52 through a pump stroke when reservoir 30 contains fluid versus when reservoir 30 is empty results in several properties that can be analyzed to determine when reservoir 30 is empty. Examples of properties that are associated with the energy required to move actuator 52 through a pump stroke that may be used to determine if reservoir 30 is empty include the shape of the waveform of the current through coil 50 for a particular pump stroke; the calculated energy required to move actuator 52 during a particular pump stroke; the voltage across capacitor 88 or coil 50 after a particular pump stroke is complete; and the amount of time required to recharge capacitor 88 after a particular pump stroke.

As can be seen by a comparison of the example waveforms of FIG. 5, waveform 110 associated with a normal pump stroke has a different shape from that of waveform 112 associated with an empty reservoir 30. For example, initial peak 128 of the empty-reservoir waveform 112 occurs slightly before initial peak 116 of normal waveform 110. In the example shown in FIG. 5, initial peak 128 of empty-reservoir waveform 112 occurs about 1.8 milliseconds after switch 92 has been closed, while initial peak 116 of normal waveform 110 does not occur until about 2.3 milliseconds after the switch closes. The amplitude of initial peak 128 of empty-reservoir waveform 112 is lower than that of initial peak 116 of normal waveform 110. In the example shown in FIG. 5, initial peak 116 of normal waveform 110 has an amplitude of about 0.49 amperes, while initial peak 128 of empty-reservoir waveform 112 has an amplitude of about 0.35 amperes. Also, the segment 130 of decreasing current immediately after initial peak 128 but before trough 132 is narrower for empty-reservoir waveform 112 than for segment 118 of normal waveform 110. In the example shown in FIG. 5, segment 130 of empty-reservoir waveform 112 lasts about 1.2 milliseconds, while segment 118 of normal waveform 110 lasts about 2.9 milliseconds. Finally, trough 132 of empty-reservoir waveform 112 occurs before trough 120 of normal waveform. In the example shown in FIG. 5, trough 132 of empty-reservoir waveform 112 occurs at about 3 ms while trough 120 of normal waveform 110 occurs at about 5.2 milliseconds.

In one example, IMD 12 is configured to analyze the waveforms of each pump stroke and to determine if the waveform is associated with a normal pump stroke such that reservoir 30 contains some therapeutic agent, or if the waveform indicates reservoir 30 is empty. IMD 12 may be configured to analyze the features described above, such as time of the initial peak 116, 128, width of the decreasing-current segment 118, 130, or the time of trough 120, 132, in order to determine if a particular waveform is associated with a normal pump stroke or a pump stroke from an empty reservoir 30.

In one example, IMD 12 is configured to store the actual shape of the current waveform in memory 36 such that processor 34 can analyze the waveform shape for each pump stroke. In one example, an analog-to-digital converter (ADC) 138 (FIG. 4) converts the output signal from coil current sensor 100 into a digital output that can be stored in memory 36 and analyzed by a processor, such as processor 34 (as shown in FIG. 4) or a processor of external programmer 20. The waveform of each pump stroke is converted by ADC 138 and then analyzed by the processor to determine if the waveform has a shape that corresponds to a normal waveform, such as normal waveform 110 shown in FIG. 5, or a shape that corresponds to a waveform of a pump stroke from an empty reservoir, such as empty-reservoir waveform 112 shown in FIG. 5.

Figure 7:
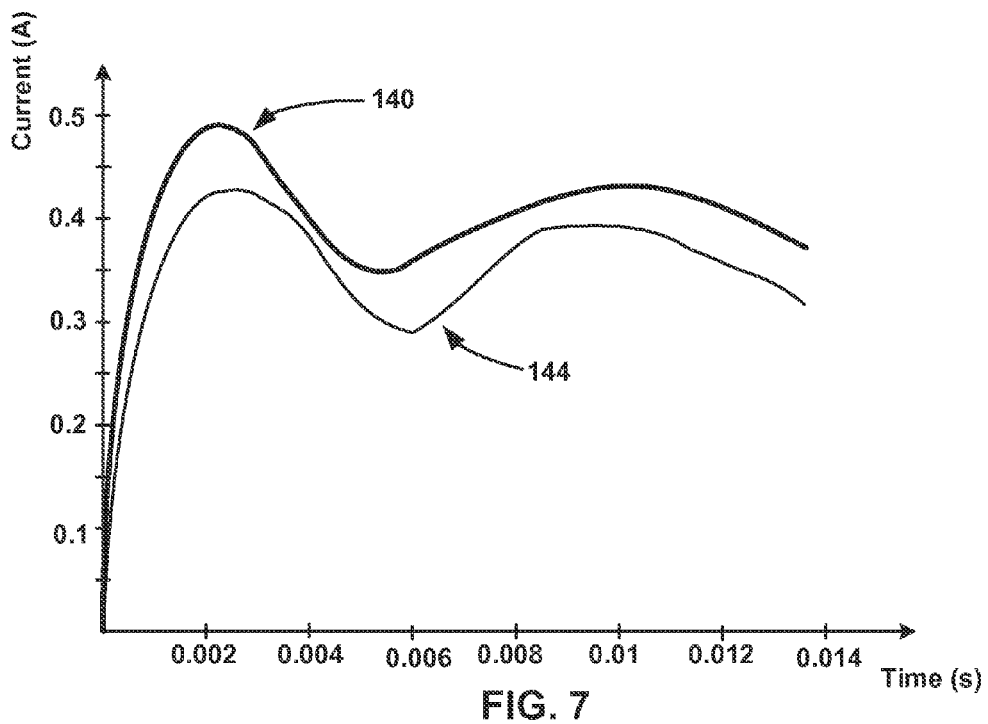
FIG. 7 is a graph showing an example current baseline waveform and an example current waveform through a coil corresponding to a pump stroke from a reservoir containing therapeutic agent.

In one example, processor 34 may analyze the waveform of a particular pump stroke by comparing it to a baseline waveform. For example, a normal pump stroke baseline waveform and/or an empty-reservoir baseline waveform may be created prior to the implantation or initial programming of IMD 12 and stored on memory 36. Processor 34 may be configured to analyze and compare the waveform shape of each pump stroke to the baseline waveforms to determine if the particular waveform corresponds to normal stroke baseline waveform, and hence a normal pump stroke, or to empty-reservoir baseline waveform, and hence that reservoir 30 is empty. In one example, shown in FIGS. 7 and 8, a normal pump stroke baseline waveform 140 and an empty-reservoir baseline waveform 142, respectively, are stored in memory 36. FIG. 7 also shows a waveform 144 that results from an actual pump stroke when reservoir 30 contains some fluid, wherein actual waveform 144 will be compared to baseline waveform 140, as described in more detail below. Similarly, FIG. 8 also shows a waveform 146 that results from an actual pump stroke from an empty or near empty reservoir 30, wherein actual waveform 146 will be compared to baseline waveform 142, as described in more detail below. Baseline waveforms 140 and 142 may be created at a time prior to the operation of IMD 12 within patient 1. For example, normal pump stroke baseline waveform 140 may be created at the time of manufacture of IMD 12, such as by filling reservoir 30 with a fluid and performing a pump stroke under controlled conditions in order to create a current waveform that will be used as baseline waveform 140. The resulting baseline waveform 140 may then be stored in memory 36 for use during operation of pump 40. Similarly, empty-reservoir baseline waveform 142 may be created at the time of manufacture of IMD 12 by performing a pump stroke when reservoir 30 is empty under controlled conditions and storing the resulting waveform as baseline waveform 142 in memory 36. Baseline waveforms 140, 142 may also be determined based on the design of IMD 12 and then saved in memory 36. Baseline waveforms 140, 142 could also be created by a clinician performing programming of IMD 12, such as via external programmer 20, using similar methods.

Figure 8:
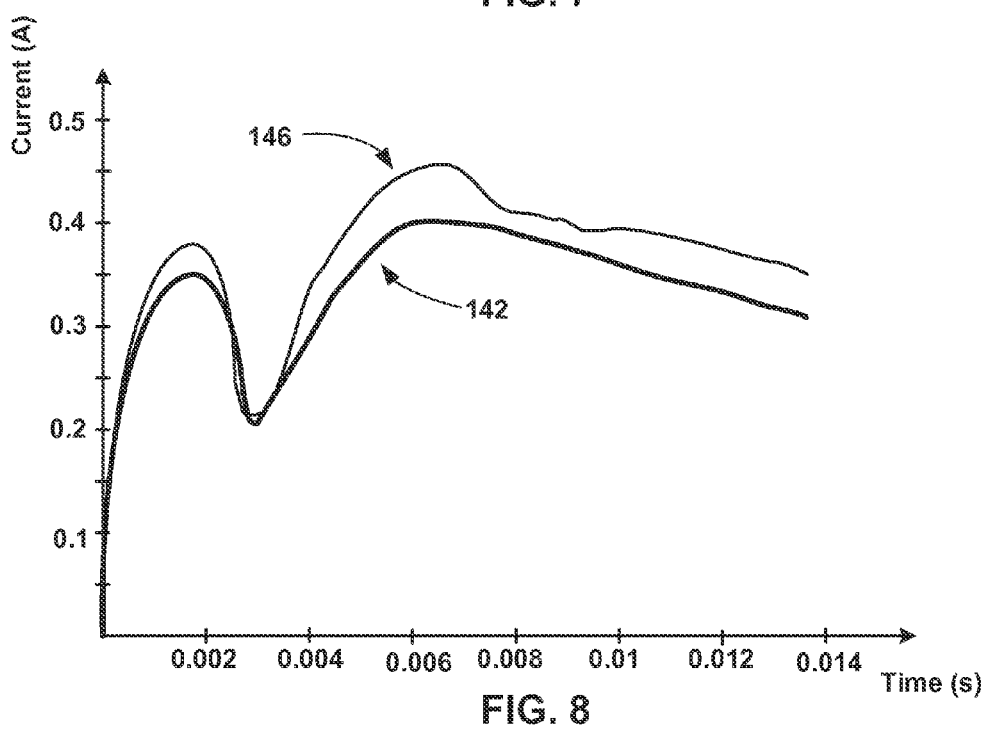
FIG. 8 is a graph showing an example current baseline waveform and an example current waveform through a coil corresponding to a pump stroke from an empty reservoir.

Although each baseline waveform 140, 142 shown in FIGS. 7 and 8 are shown as a single waveform line, the term "baseline waveform," as it is used herein, may include a set of waveform shapes or a range of waveform shapes that are analyzed and compared to the waveform shape of each pump stroke. For example, empty-reservoir baseline waveform 142 may comprise a plurality of waveform shapes that together form a range of waveform shapes that correspond to an empty reservoir. The waveform shape of each pump stroke may be analyzed such that if the pump-stroke waveform shape falls within the range of empty-reservoir baseline waveform 142, the pump stroke will be determined to be from an empty reservoir 30. In one example, only an empty-reservoir baseline waveform 142 is stored in memory 36. After each pump stroke, it is determined whether the pump-stroke waveform corresponds to empty-reservoir baseline waveform 142, such as by falling within a range of waveform shapes that comprise empty-reservoir baseline waveform 142. If the pump-stroke waveform does correspond to empty-reservoir baseline waveform 142, such as by falling within the range, then reservoir 30 will be determined to be empty. If the pump-stroke waveform does not correspond to empty-reservoir baseline waveform 142, such as by falling outside of the range, then reservoir 30 will be determined to contain therapeutic agent (e.g., reservoir 30 is not empty).

IMD 12 stores the waveform of each pump stroke in order to compare to the baseline waveforms 140, 142. In one example, IMD 12 stores the waveform of each pump stroke by storing the digital values of the current through coil 50 as a function of time, as measured by coil current sensor 100 and converted by ADC 138, in memory 36. IMD 12 may also store the baseline waveforms as a series of current values as a function of time. For example, FIG. 7 shows a visual representation of an actual waveform 144 of a recent pump stroke that is stored on memory 36. Even though baseline waveform 140 and actual waveform 144 are not identical, processor 34 may be configured to compare the shapes of both waveforms and determine that the actual waveform 144 of the recent pump stroke corresponds to the shape of baseline waveform 140. In such a case, processor 34 may determine that reservoir 30 contains some therapeutic agent. At a later time, however, IMD 12 may determine that the most recent pump stroke has an actual waveform 146, shown in FIG. 8. Processor 34 may determine that waveform 146 corresponds to the shape of empty-reservoir baseline waveform 142, even though waveform 146 and baseline waveform 142 are not identical. In such a case, processor 34 may determine that reservoir 30 is empty. In one example, processor 34 may compare a stored waveform to a baseline waveform by performing comparison calculations to determine if the waveform and baseline waveform are within a predetermined variance of one another. For example, processor 34 may perform a root-mean-square analysis of a recent actual waveform 144, 146 and each baseline waveform 140, 142 stored in memory, wherein the recent actual waveform 144, 146 may be determined to correspond to a particular baseline waveform 140, 142 when the root mean square between the two waveforms is within a certain predetermined threshold.

In another example, certain landmarks of the waveform may be compared to baseline waveforms 140, 142 to determine if actual waveform 144, 146 indicates reservoir 30 is empty. For example, as shown in FIG. 5, the current value at peak 116, 128 is less for an empty waveform 112 than for a normal waveform 110. Similarly, the current value at trough 120, 132 may be different between normal waveform 110 and empty waveform 112. Therefore, the current value of the initial peak or the trough of actual waveform 144, 146 may be compared to that of baseline waveforms 140, 142 to determine if actual waveform 144, 146 corresponds to an empty reservoir 30. In another example, the width between peak 116, 128 and trough 120, 132 may be narrower for an empty waveform 112 than it is for a normal waveform 110 (see FIG. 5). Processor 34 may be configured to determine that the width between peak 116, 128 and trough 120, 132 corresponds to a pump stroke from an empty reservoir 30.

In another example, processor 34 may determine a number of comparison points at set times for actual waveform 144, 146 and for baseline waveform 140, 142, such as by determining the current value at set time points, for example, after every millisecond or every half of a millisecond. Then, processor 34 may determine the difference between the comparison point for actual waveform 144, 146 and baseline waveform 140, 142 at each time point. Processor 34 may determine that actual waveform 144, 146 corresponds to baseline waveform 140, 142 if a predetermined number of the comparison points from actual waveform 144, 146 are within a predetermined variance from the corresponding comparison points from baseline waveform 140, 142. For example, processor 34 may determine comparison points for actual waveform 146 at 1 ms, 2 ms, 3 ms, 4 ms, 5 ms, 6 ms, 7 ms. 8 ms, 9 ms, and 10 ms for a total of ten comparison points that can be compared to comparison points for the same time points on baseline waveform 142. Processor 34 may be configured to determine how many comparison points from actual waveform 146 are within a predetermined threshold, e.g., within about 0.01 amps, from the corresponding comparison points from baseline waveform 142. Processor 34 may determine that actual waveform 146 corresponds to empty-reservoir baseline waveform 142 when the number of comparison points that are within the predetermined threshold is equal to or greater than a certain number. For example, processor 34 may determine that actual waveform 146 corresponds to empty-reservoir baseline waveform 142, and thus determine that reservoir 30 is empty, when at least 50%, or at least five of ten, of the comparison points are within the predetermined threshold. In another example processor 34 may determine that reservoir 30 is empty when at least 60%, or at least six of ten, of the comparison points are within the predetermined threshold. In another example, processor 34 may determine that reservoir 30 is empty when at least 75%, or at least eight of ten, of the comparison points are within the predetermined threshold. In another example, processor 34 may determine that reservoir 30 is empty when at least 80%, or at least eight of ten, of the comparison points are within the predetermined threshold. In another example, processor 34 may determine that reservoir 30 is empty when at least 90%, or at least nine of tell, of the comparison points are within the predetermined threshold. Processor 34 may also be configured to determine that reservoir 30 is empty only when 100%, or all tell of ten, of the comparison points are within the predetermined threshold.

In another example, the energy that is actually passed through coil 50 in order to move actuator 52 through each pump stroke may be calculated, and the calculated energy may be used to determine whether reservoir 30 contains some therapeutic agent or is empty. As described above, the amount of energy required to move actuator 52 through a normal pump stroke is larger than the amount of energy required for a pump stroke from an empty reservoir 30 because when reservoir 30 is empty, actuator 52 does not have to move any fluid. The energy that passes through coil 50 can be determined by several methods. In one example, IMD 12 includes a voltage sensor 102 that measures the voltage across coil 50. Although voltage sensor 102 is shown as measuring the voltage directly across coil 50, a voltage sensor may be placed across other portions of the circuit powering coil 50. For example, since the resistance of coil current sensor 100 and switching device 92 are each quite low, the voltage across capacitor 88 can be measured, such as with the capacitor voltage sensor 104 shown in FIG. 4, and the voltage across capacitor 88 can be assumed to be approximately equal to the voltage across coil 50.

The measured voltage across coil 50, referred to herein as $V_{Coil}$, can be used to calculate the total energy that passes through coil 50 during a specific time. When energy is being provided by a capacitor, such as capacitor 88, and it can be assumed that the capacitance of the capacitor is constant, the energy provided to coil 50 from capacitor 88, $W_{Coil}$, can be calculated according to Equation 1:

$$W_{Coil} = \frac{1}{2}C(V^2_{Coil,Start} - V^2_{Coil,End}) \qquad [1]$$

where C is the capacitance of capacitor 88, $V_{Coil,Start}$ is the voltage across coil 50 at the start of the pump stroke and $V_{Coil,End}$ is the voltage across coil 50 at the end of the pump stroke. IMD 12 may be configured so that the energy provided to coil, $W_{Coil}$, is calculated for each pump stroke so that it can be determined whether the energy provided to coil 50 corresponds to a high-energy normal pump stroke, wherein it can be assumed that reservoir 30 contains some therapeutic agent, or a low-energy pump stroke, wherein it can be assumed that reservoir 30 is empty.

Figure 6:
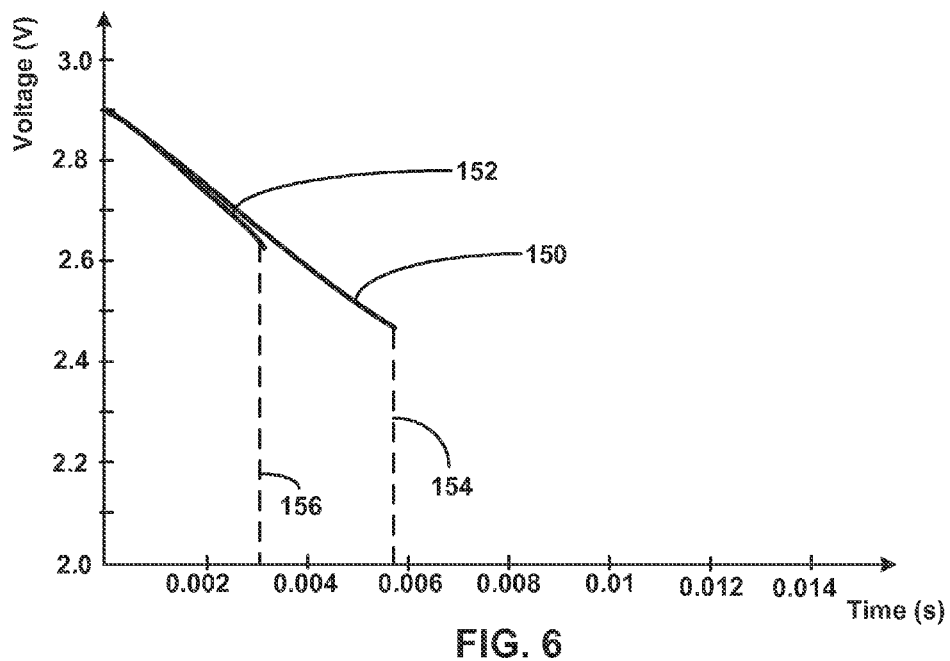
FIG. 6 is a graph showing example voltage waveforms across a coil of the medical pump for a pump stroke from a reservoir containing therapeutic agent and a pump stroke from an empty reservoir.

FIG. 6 shows examples of the waveforms for the voltage across coil 50. Waveform 150 is an example of the voltage across coil 50 for a normal pump stroke while waveform 152 is an example of the voltage across coil 50 for a pump stroke from an empty reservoir 30. For ease of discussion, voltage waveform 150 results from the same normal pump stroke that produced current waveform 110 in FIG. 5, while voltage waveform 152 results from the same empty-reservoir pump stroke that produced current waveform 112 in FIG. 5. IMD 12 may also include means for determining when actuator 52 has reached the end of a pump stroke, such that switching device 92 may be opened as soon as the end of stroke is detected in order to conserve energy. In the example of FIGS. 5 and 6, IMD 12 determines that the end of a normal pump stroke occurs at the time represented by line 154, while the end of a pump stroke from an empty reservoir 30 occurs at the time represented by line 156. At each of these times 154, 156 when the end of each pump stroke is determined, switching device 92 is opened so that there is no longer any current flowing through coil, and hence there is no longer a voltage across coil 50.

In the example of FIG. 6, coil voltage sensor 102 can be used to determine the values that will be used in Equation 1. In one example, capacitor 88 has a capacitance of about 4 millifarads, voltage waveform 150 for a normal pump stroke shows an initial voltage of about 2.9 volts when switching device 92 is closed and current begins flowing through coil 50, and a final voltage of about 2.35 volts. According to Equation 1, therefore, the energy provided by capacitor 88 to coil 50 for a normal pump stroke is about 5.8 millijoules. Voltage waveform 152 for an empty-reservoir pump stroke shows the same initial voltage of about 2.9 volts, but has a final voltage of about 2.63 volts. According to Equation 1, therefore, the energy provided by the same 4 millifarad capacitor 88 for a pump stroke from an empty reservoir 30 is about 3 millijoules.

In another example, the energy supplied to coil 50 can be calculated by using coil current sensor 100 in conjunction with coil voltage sensor 102 to determine the total energy required for each pump stroke. In such examples instead of employing Equation 1, the energy across coil 50, $W_{Coil}$, may be calculated according to Equation 2.

$$W_{Coil} = \int_{t1}^{t2} V_{Coil}(t) \cdot I_{Coil}(t) dt \qquad [2]$$

As can be seen, Equation 2 requires integration of the product of two time-varying functions, $V_{Coil}(t)$ and $I_{Coil}(t)$. As described above, IMD 12 may include an analog-to-digital converter (ADC) 138 that can convert the analog output from coil current sensor 100 to a digital output that can be analyzed by a processor, such as processor 34 of IMD 12 or a processor of external programmer 20, to determine if reservoir 30 is empty. ADC 138 may also be used to convert an analog output from coil voltage sensor 102 to a digital output. The digital outputs of the current values from coil current sensor 100 and coil voltage sensor 102 can be used by processor 34 to perform the integration of Equation 2 in order to calculate the energy that is provided to coil 50.

As can be seen from the example of FIG. 6, significantly less energy is required to drive actuator 52 when reservoir 30 is empty as compared to when reservoir 30 contains the therapeutic agent. IMD 12 can be programmed to recognize when the energy required to drive actuator 52 through a particular pump stroke corresponds to a reservoir 30 that is empty. In one example, processor 34 is configured so that when the calculated energy supplied to coil 50 for a particular pump stroke is within a certain threshold of a first, higher calculated energy, processor 34 will determine that the pump stroke is a normal pump stroke and that reservoir 30 contains some therapeutic fluid. Processor 34 may also be configured so that when the calculated energy supplied to coil 50 is within a certain threshold of a second, lower calculated energy, processor 34 will determine that the pump stroke is one associated with an empty reservoir 30.

A normal pump stroke generally may vary from the expected or average energy for a normal pump stroke. In one example, the energy required for a normal pump stroke may vary between about 10% to about 40% of the expected average energy. Therefore, processor 34 may be configured to determine that a pump stroke is a normal pump stroke when the energy required for the pump stroke varies by less than about 10% to about 40% of the average expected energy of a normal pump stroke, such as the 5.8 millijoules calculated above for the example of FIG. 6. In one example, processor 34 may determine that a pump stroke is a normal pump stroke when it has an energy between about 0.5 millijoules and about 2.3 millijoules, or between about 10% and about 40% of the 5.8 millijoules expected of a normal pump stroke.

In one example, processor 34 may be configured to determine that a pump stroke is from an empty reservoir 30 when the energy required for the pump stroke is less than or equal to a threshold value, wherein processor 34 may be confident that if the energy required for a pump stroke is below the threshold value then it probably corresponds to a pump stroke from an empty reservoir. As noted above, a "normal" pump stroke, e.g., a pump stroke that is not from an empty reservoir, may vary from the average expected value by between about 10% and about 40% of the expected value. The threshold value may be selected to correspond to a decrease in energy from a normal pump stroke that is larger than this expected or assumed pump energy variation. For example, if the energy required for a normal pump stroke is expected to vary by about 20% from a "normal" average expected value, then the threshold value may be selected to represent a decrease from the normal expected value that is greater than 20%. In such an example, the threshold value may be selected to be at least about 30% less than normal expected value, such as at least about 40% less than the normal expected value, for example about 50% less than the normal expected value. For the example wherein an average normal expected value is about 5.8 millijoules, described above with respect to FIG. 6, then processor 34 may be configured to determine that a pump stroke is from an empty reservoir when the energy required for the pump stroke is less than a threshold value of about 4.1 millijoules (about 30% less than, or about 70% of 5.8 millijoules). In another example, processor 34 may be configured to determine that a pump stroke is from an empty reservoir when the energy required for the pump stroke is less than a threshold value of about 3.5 millijoules (about 40% less, or about 60% of 5.8 millijoules). In another example, processor 34 may be configured to determine that a pump stroke is from an empty reservoir when the energy required for the pump stroke is less than a threshold value of about 2.9 millijoules (about 50% less, or about 50% of 5.8 millijoules).

In one example, processor 34 may determine whether reservoir 30 contains the therapeutic agent or is empty based on a set of pump strokes by determining how many of the plurality of pump strokes indicate that reservoir 30 contains fluid and how many of the set of pump strokes indicate that reservoir 30 is empty. In one example, when a predetermined number of the set of pump strokes indicate that reservoir 30 is empty, processor 34 will determine that reservoir 30 is empty. For example, processor 34 may keep a moving window record of the most recent pump strokes, e.g., the last 10 pump strokes. The predetermined number of pump strokes and the number of pump strokes to be included in the set that are used by processor 34 to determine if reservoir 30 is empty may depend on the therapy rate being delivered by IMD 12, e.g., the predetermined number and the set may depend on the rate of pump strokes delivered by IMD 12 over time, as well as the under-infusion risks and side effects associated with the therapeutic agent being delivered. For example, if IMD 12 is programmed to deliver about 48 pump strokes per day, or about two pump strokes per hour, number of pump strokes in the moving window set and the predetermined number may be set to be fairly low, e.g. a moving window of 4 pump strokes (about two hours of delivery) while the predetermined number may be 2 pump strokes (50% of the moving window), so that a patient will know about an empty reservoir 30 within two hours from its emptying.

However, if IMD 12 delivers at a faster rate, such as 480 pump strokes per day, or on average about every three minutes, the moving window and the predetermined number may be set to be larger, such as a moving window set of 10 pump strokes and a predetermined number of seven. In such a case, IMD 12 can be more confident that reservoir 30 is empty (because 70%, rather than 50% of recent pump strokes indicated an empty reservoir), while still determining that reservoir 30 is empty within 30 minutes (10 pump strokes).

When the predetermined number of the set of most recent pump strokes have an energy that is within a predetermined threshold of the energy expected from an empty reservoir 30, then processor 34 may determine that reservoir 30 is empty. In one example, processor 34 may determine that reservoir 30 is empty when at least about 50%, e.g., five of the ten, of the recent pump strokes are within the predetermined threshold of the expected empty-reservoir energy. In another example, processor 34 may determined that reservoir 30 is empty when at least about 60%, e.g., six out of ten, of the pump strokes are within the predetermined threshold, such as at least about 75%, e.g., eight out of ten, for example, at least about 80%, e.g., eight out of ten, and in one example at least about 90%, e.g., nine out of ten, of the pump strokes are within the predetermined threshold. In one example, processor 34 may only determine that reservoir 30 is empty when 100% of the plurality of recent pump strokes, e.g., all ten out of ten, are within the predetermined threshold of an expected empty reservoir pump stroke. If fewer than the predetermined number or percentage of pump strokes are within the predetermined threshold of the expected energy for an empty-reservoir pump stroke, then processor 34 may determine that reservoir 30 is not empty, e.g., that reservoir 30 contains some therapeutic agent.

In another example, processor 34 may determine that reservoir 30 is empty when a predetermined number of consecutive pump strokes have an energy that is within a predetermined threshold from the expected energy of a pump stroke from an empty reservoir 30. The predetermined number of consecutive pump strokes that will cause processor 34 to determine that reservoir 30 is empty may depend on the therapy rate being delivered by IMD 12 as well as the under-infusion risks and side effects associated with the therapeutic agent being delivered. In one example, processor may determine that reservoir 30 is empty when at least 3 consecutive pump strokes require an energy that is within the predetermined threshold of the expected energy of an empty-reservoir pump stroke, such as at least 5 consecutive pump strokes, for example at least 10 consecutive pump strokes. If fewer than the predetermined number of pump strokes has an energy that is within the predetermined threshold from the expected empty-reservoir energy, then processor 34 may determine that reservoir 30 contains some therapeutic agent.

The value of the predetermined threshold, e.g., the difference between the expected energy of a pump stroke and the actual energy of a pump stroke that will indicate to processor 34 whether a particular pump stroke is from an empty reservoir 30, and the expected energy for a particular kind of pump stroke (e.g. an empty reservoir or non-empty reservoir pump stroke), may depend on the specific fluid being delivered. For example, characteristics of the therapeutic agent being delivered, such as the molecular weight of a drug being delivered or a viscosity of the therapeutic agent fluid, may affect the amount of energy required for each pump stroke to deliver the therapeutic agent. Therefore, the expected energy or the predetermined threshold for a normal pump stroke or an empty-reservoir pump stroke may be altered depending on the fluid being delivered. Another factor that may affect the predetermined threshold or the expected energy is the battery depletion over the life of IMD 12.

In another example, rather than calculating the actual energy that is provided to coil 50, voltage sensor 102 may be used to determine the voltage change across coil 50 during each pump stroke, and processor may determine whether the voltage change corresponds to a normal pump stroke or a pump stroke from an empty reservoir 30. In one example, described above, IMD 12 may be configured so that the voltage across coil 50 at the start of a pump stroke is generally the same such that the ending voltage across coil 50 after a pump stroke may be used as an indicator of the voltage change to determine whether the pump stroke was a normal pump stroke or a pump stroke from an empty reservoir 30. As described above, after a normal pump stroke, the ending voltage across coil 50 may be expected to be lower than the voltage after a pump stroke from an empty reservoir 30. As shown in the example of FIG. 6, the ending voltage of the normal voltage waveform 150 is about 2.47 volts while the ending voltage of the empty-reservoir voltage waveform 152 is about 2.65 volts. In another example, the starting voltage across coil 50 may be variable, such that voltage sensor 102 may be used to determine the voltage across coil 50 before the pump stroke and after the pump stroke in order to calculate the voltage change.

In one example, processor 34 is configured so that when the voltage change across coil 30 for a particular pump stroke is within a certain threshold of a first, larger voltage change, processor 34 will determine that the pump stroke was a normal pump stroke and that reservoir 30 contains some therapeutic fluid. Processor 34 may also be configured so that when the voltage change across coil 30 after a particular pump stroke is within a certain threshold of a second, smaller voltage change, processor 34 will determine that the pump stroke is one associated with an empty reservoir 30. In one example, wherein the starting voltage across coil 50 is a constant, fixed starting voltage, a pump stroke may be determined to be a normal pump stroke when the ending voltage across coil 50 is within a certain threshold of a first, lower ending voltage, and a pump stroke may be determined to be from an empty reservoir when the ending voltage across coil 50 is within a certain threshold of a second, higher ending voltage.

In one example, processor 34 may be configured to determine that a pump stroke is a normal pump stroke when the voltage change across coil 50 after a pump stroke is the voltage that would be expected by a pump stroke within the energy variation described above (e.g., with an energy variation of about 20%, about 30%, or about 40%). For example, if the energy for a normal pump stroke is expected to vary by about 20%, then the voltage change across coil 50 may be expected to vary by between about 15% and about 25% of the expected voltage change. In one example, the voltage change across coil 30 may be determined to correspond to a normal pump stroke if it is within between about 0.01 volts and about 0.3 volts of an expected ending voltage after a normal pump stroke, such as the 2.47 volts shown for the example of FIG. 6.

In one example, processor 34 may be configured to determine that a pump stroke is from an empty reservoir 30 when the voltage change across coil 50 is less than would be expected due to the energy variation of a normal pump stroke. In one example, wherein the starting voltage across coil 50 is fixed, processor 34 may be configured to determine that a pump stroke is from an empty reservoir 30 when the ending voltage change across coil 50 is higher than would be expected due to the energy variation of a normal pump stroke. For example, if a 20% variation in energy is expected for normal pump strokes, processor 34 may be configured to determine when the voltage change across coil 50 is greater than or equal to the energy expected for a 30% variation, wherein the extra 10% (from 20% to 30%) may be included to ensure the voltage change is not due to energy variation. In one example, wherein the expected voltage change for a normal pump stroke is 0.43 V (2.9 V starting voltage to a 2.47 ending voltage in FIG. 6), a 30% energy variation may be expected to result in a voltage change that is about 40% less than the voltage change from a normal pump stroke, or a threshold voltage change of about 0.26 volts and a threshold ending voltage of about 2.64 volts for the example values from FIG. 6. In another example, wherein a 40% change in the energy for a pump stroke is used to calculate the threshold values, the threshold change is about 50% less than the voltage change for a normal pump stroke, or a voltage change of about 0.21 volts and an ending voltage of about 2.69 volts using the example values from FIG. 6. In another example, wherein a 50% change in the energy for a pump stroke is used to calculate the threshold values, the threshold change is about 65% less than the voltage change for a normal pump stroke, or a voltage change of about 0.15 volts and an ending voltage of about 2.75 volts using the example values from FIG. 6. Processor 34 may be configured so that any time the voltage change is greater than the threshold voltage change (e.g. the 0.26 volts for the 30% example; 0.21 volts for the 40% example, and 0.15 volts for the 50% example), or in the case of a fixed starting voltage, any time the ending voltage across coil 50 is less than the threshold ending voltage (e.g. 2.64 volts for the 30% example, 2.69 volts for the 40% example, and 2.75 volts for the 50% example), then processor 34 will determine that the pump stroke was a normal pump stroke. If the voltage change is less than threshold voltage change, or in the case of a fixed starting voltage if the ending voltage is greater than the threshold ending voltage, processor 34 may determine that the pump stroke came from an empty reservoir 30.

In one example, rather than analyzing individual pump strokes, processor 34 may be configured to determine that reservoir 30 is empty when the ending voltage from each of a predetermined percentage of the plurality of pump strokes indicate that reservoir 30 is empty. In one example, processor 34 may determine reservoir 30 is empty when at least about 50%, of a plurality of recent pump strokes are within a predetermined threshold of the expected ending voltage after an empty-reservoir pump stroke, for example when at least about 60%, at least about 75%, at least about 80%, and at least about 90% of the pump strokes are within the predetermined threshold of the expected ending voltage for an empty-reservoir pump stroke. In one example, processor 34 may only determine that reservoir 30 is empty when 100% of the recent pump strokes are within the predetermined threshold of the expected ending voltage for an empty-reservoir pump stroke. If fewer than the predetermined number or percentage of pump strokes are within the predetermined threshold of the expected ending voltage for an empty-reservoir pump stroke, then processor 34 may determine that reservoir 30 is not empty, e.g., that reservoir 30 contains some therapeutic agent.

Processor 34 may also be configured to determine when a predetermined number of consecutive pump strokes result in an ending voltage across coil 50 that is within the expected ending voltage for an empty-reservoir pump stroke. The predetermined number of consecutive pump strokes that will cause processor 34 to determine that reservoir 30 is empty may depend on the therapy rate being delivered by IMD 12 as well as the under-infusion risks and side effects associated with the therapeutic agent being delivered. In one example, processor 34 may determine that reservoir 30 is empty when at least 3 consecutive pump strokes result in an ending voltage across coil 50 that is within the predetermined threshold of the expected energy of an empty-reservoir pump stroke, such as at least 5 consecutive pump strokes, for example at least 10 consecutive pump strokes. If fewer than the predetermined number of pump strokes result in an ending voltage across coil 50 that is within the predetermined threshold from the expected empty-reservoir ending voltage, then processor 34 may determine that reservoir 30 contains some therapeutic agent.

The ending voltage across coil 50 and the variance from the ending voltage may depend on characteristics of the fluid being delivered, such as the molecular weight of a drug being delivered or a viscosity of the therapeutic agent fluid. Therefore, the expected ending voltage for a normal pump stroke or an empty-reservoir pump stroke may be altered depending on the fluid being delivered. Another factor that may affect the expected ending voltage is the battery depletion over the life of IMD 12.

In another example, rather than calculating the energy supplied to coil 50 by analyzing properties of coil 50 itself, IMD 12 may be configured to detect and analyze properties of capacitor 88 associated with the energy required to drive actuator 52 through a pump stroke. For example, a sensor may be used to determine a property associated with the energy supplied by capacitor 88. In one example, capacitor sensor 104 of the example of FIG. 4 is used to determine the time it takes to recharge capacitor 88 after is has been discharged to provide a pump stroke. The amount of time to recharge capacitor 88 is directly proportional to the energy required to drive actuator 52 through a complete pump stroke. For example, as described above a normal pump stroke when reservoir 30 contains some amount of the therapeutic agent requires more energy than a pump stroke from an empty reservoir 30. Therefore, the recharge time after a normal pump stroke will be longer than the recharge time after a pump stroke from an empty reservoir 30.

Figure 9:
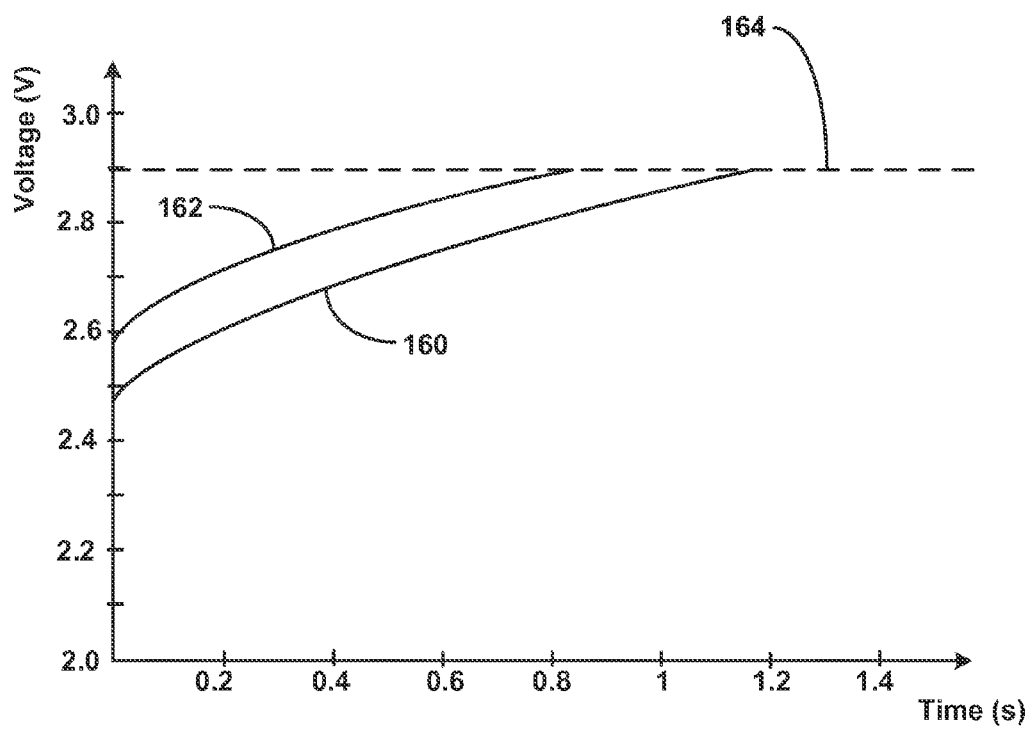
FIG. 9 is a graph showing example recharge curves for recharging a capacitor after a pump stroke from a reservoir containing therapeutic agent and after a pump stroke from an empty reservoir.

FIG. 9 shows an example recharge curve 160 of the voltage across capacitor 88 as it is recharged after a normal pump stroke, and an example recharge curve 162 of the voltage across capacitor 88 as it is recharged after a pump stroke from an empty reservoir 30. Recharge curves 160 and 162 are created from the measurement of the voltage across capacitor 88 that is provided by capacitor voltage sensor 104. The "recharge time" may be calculated by determining the amount of time from the point when switching device 90 between battery 86 and capacitor 88 is closed, represented by t=0 in FIG. 9, and the time when the voltage across capacitor 88 reaches a predetermined threshold voltage. In the example of FIG. 9, the threshold voltage is about 2.9 volts, represented by line 164. As can be seen in the example of FIG. 9, the voltage across capacitor 88 after a normal pump stroke is lower than the voltage after an empty-reservoir pump stroke because more energy was required for the normal pump stroke. Because of this, the recharge time for recharge curve 160 is longer than the recharge time for recharge curve 162. In the example of FIG. 9, recharge curve 160 after a normal pump, stroke recharges capacitor 88 from an initial voltage of about 2.34 volts to the final threshold voltage of 2.9 volts in about 1.18 seconds. Recharge curve 162 after a pump stroke from an empty reservoir 30 recharges capacitor 88 from an initial voltage of about 2.58 volts to the final threshold voltage of 2.9 volts in about 0.84 seconds.

The recharge time of capacitor 88 also may be determined by comparing the voltage across capacitor 88 to the voltage provided by battery 86. Generally speaking, when a capacitor, such as capacitor 88, is charged by a direct current power supply, such as battery 86, it can be considered "charged" when the voltage across the capacitor is equal to the voltage provided from the power source. Therefore, the voltage measured by capacitor voltage sensor 104 can be compared to the voltage provided by battery 86 to determine at what point the voltages are equal to each other or when the voltages are within a predetermined threshold from each other. The point in time when this state is reached can be considered the point when capacitor is recharged 88, which in turn can be used to calculate the recharge time required to recharge capacitor.

Capacitor sensor 104 may be a type of sensor other than a voltage sensor while still being used to determine the recharge time of capacitor 88. For example, capacitor sensor 104 may be a current sensor that determines the current passing through capacitor 88. The current flowing through a capacitor exponentially decreases over time when it is being charged by a direct current power source like battery 86, eventually reaching a current of essentially zero. Thus, when the current sensed by capacitor sensor 104 reaches zero, or falls below a predetermined threshold level that is sufficiently close to zero, capacitor 88 may be considered to be "recharged."

Voltage capacitor sensor 104 may be configured to determine the recharge time of capacitor 88 after each pump stroke. When the recharge time decreases below the recharge time for a normal pump stroke, sensor 104 may determine that reservoir is empty. In one example, the recharge time after a normal pump stroke may be between about 1.0 second and about 1.2 seconds. In another example, the recharge time after a normal pump stroke may be between about 1.1 seconds and about 1.2 seconds. In yet another example, the recharge time after a normal pump stroke may be about 1.15 seconds. Processor 34 may be configured to determine when the recharge time of capacitor 88 falls within one of these ranges, and if so to determine that the pump stroke was a normal pump stroke and that reservoir 30 contains the therapeutic agent. In one example, the recharge time after a pump stroke from an empty reservoir 30 may be between about 0.8 seconds and about 1.0 second. In another example, the recharge time after a pump stroke from an empty reservoir 30 may be between about 0.8 seconds and about 0.9 seconds. In yet another example, the recharge time after a pump stroke from an empty reservoir 30 may be about 0.85 seconds.

In another example, rather than using the time to recharge capacitor 88, the initial voltage across capacitor 88 after a pump stroke is complete, but before recharging may be used to detect an empty reservoir 30 or that reservoir 30 contains therapeutic fluid. As described above, IMD 12 may be configured so that capacitor 88 is recharged to the same starting voltage, so that the voltage across capacitor 88 after a particular pump stroke may provide guidance as to whether the pump stroke was a normal pump stroke or a pump stroke from an empty reservoir 30. After a normal pump stroke, the ending voltage across capacitor 88 may be expected to be lower than the voltage after a pump stroke from an empty reservoir 30. As shown in the example of FIG. 9, the voltage across capacitor 88 after a pump stroke but before recharging (e.g. the voltage at time=0 in FIG. 9) for the normal voltage recharge curve 160 is about 2.35 volts while the voltage across capacitor 88 after a pump stroke but before recharging for the empty-reservoir recharge curve 162 is about 2.58 volts. In one example, processor 34 is configured so that when the voltage across capacitor 88 after a particular pump stroke is within a certain threshold of a first, lower ending voltage, processor 34 will determine that the pump stroke was a normal pump stroke and that reservoir 30 contains some therapeutic fluid. Processor 34 may also be configured so that when the voltage across capacitor 88 after a particular pump stroke is within a certain threshold of a second, higher calculated energy, processor 34 will determine that the pump stroke is one associated with an empty reservoir 30.

In one example, processor 34 may be configured to determine that a pump stroke is a normal pump stroke when the starting voltage across capacitor 88 after a pump stroke but before recharging is within between about 0.01 volts and about 0.33 volts of an expected starting voltage after a normal pump stroke, such as the 2.35 volts shown for the example of FIG. 9. In one example, processor 34 may be configured to determine that a pump stroke is from an empty reservoir 30 when the starting voltage across capacitor 88 after a pump stroke but before recharging is within between about 0.01 volts and about 0.33 volts of an expected starting voltage after a pump stroke from an empty reservoir, such as the 2.58 volts shown for the example of FIG. 9. Threshold voltages based on expected initial voltage across capacitor 88 before recharging for different variations of energy required for a pump strokes, such as the 20% variation, 30% variation, or 40% variation described above, may be used similar to the thresholds described above with respect to the voltage change and ending voltage across coil 50.

In one example, rather than analyzing individual pump strokes, processor 34 may be configured to determine that reservoir 30 is empty when the starting voltage across capacitor 88 from a predetermined percentage of the plurality of pump strokes indicate that reservoir 30 is empty, such as when at least about 50%, at least about 60%, at least about 75%, at least about 80%, or at least about 90%, or 100% of a plurality of recent pump strokes are within a predetermined threshold of the expected starting voltage for an empty-reservoir pump stroke. Processor 34 may also be configured to determine when a predetermined number of consecutive pump strokes result in a starting voltage across capacitor 88 that is within a predetermined threshold of the expected starting voltage for an empty-reservoir pump stroke, such as at least 5 consecutive pump strokes, at least 7 consecutive pump strokes, or at least 10 consecutive pump strokes. If fewer than the predetermined number or percentage of pump strokes are within the predetermined threshold of the expected starting voltage for an empty-reservoir pump stroke, then processor 34 may determine that reservoir 30 is not empty, e.g., that reservoir 30 contains some therapeutic agent.

The starting voltage across capacitor 88 and the variance from the starting voltage may depend on characteristics of the fluid being delivered, such as the molecular weight of a drug being delivered or a viscosity of the therapeutic agent fluid. Therefore, the expected starting voltage across capacitor 88 for a normal pump stroke or an empty-reservoir pump stroke may be altered depending on the fluid being delivered. Another factor that may affect the expected starting voltage is the battery depletion over the life of IMD 12.

In another example, the amount of energy actually supplied to recharge capacitor 88 may be calculated. Similar to Equation 1 described above, the energy actually supplied to capacitor 88, $W_{Cap.}$, may be determined by Equation 3:

$$W_{Cap.} = \frac{1}{2}C(V_{Cap.,End}^2 - V_{Cap.,Start}^2) \quad [3]$$

where C is the capacitance of capacitor 88, $V_{Cap., Start}$ is the voltage across capacitor 88 at the start of recharging, and $V_{Cap., End}$ is the voltage across capacitor 88 at the end of recharging. As with the example using Equation 1 described above, IMD 12 may be configured so that the energy needed to recharge capacitor 88, $W_{Cap.}$, is calculated after each pump stroke so that it can be determined whether the recharge energy corresponds to a high-energy normal pump stroke, wherein it can be assumed that reservoir 30 contains some therapeutic agent, or a low-energy pump stroke, wherein it can be assumed that reservoir 30 is empty.

Referring to the example waveforms for the voltage across capacitor 88 during recharging shown in FIG. 9, capacitor voltage sensor 104 may be used to determine the values that will be used in Equation 3. In one example, capacitor 88 has a capacitance of about 4 millifarads, recharge curve 160 for a recharge after a normal pump stroke shows a starting voltage of about 2.35 volts when switching device 90 is closed and capacitor 88 begins to recharge, and a final voltage of about 2.9 volts. According to Equation 3, the energy provided to recharge capacitor 88 after this normal pump stroke is about 5.8 millijoules. Recharge curve 162 for recharging capacitor 88 after an empty-reservoir pump stroke shows an initial voltage of about 2.58 volts, and a final voltage of about 2.9 volts. According to Equation 3, the energy needed to recharge the same 4 millifarad capacitor 88 for a pump stroke from an empty reservoir 30 is about 3.5 millijoules.

In one example, processor 34 is configured so that when the calculated energy required to recharge capacitor 88 after a particular pump stroke is within a certain threshold of a first, higher calculated energy, processor 34 will determine that the pump stroke is a normal pump stroke and that reservoir 30 contains some therapeutic fluid. Processor 34 may also be configured so that when the calculated energy required to recharge capacitor 88 is within a certain threshold of a second, lower calculated energy, processor 34 will determine that the pump stroke is one associated with an empty reservoir 30.

In one example, processor 34 may be configured to determine that a pump stroke is a normal pump stroke when the energy required to recharge capacitor 88 is within about 0.1 millijoules of an expected recharge energy of a normal pump stroke and about 3 millijoules of an expected recharge energy of a normal pump stroke, such as the 5.8 millijoules calculated above for the example of FIG. 9. In another example, processor 34 may be configured to determine that a pump stroke is a normal pump stroke when the recharge energy for capacitor 88 is within between about 5% and about 50% of the expected recharge energy for a normal pump stroke (e.g., for an expected recharge energy of 5.8 millijoules, between about 0.3 millijoules (~5% of 5.8 mJ) and about 2.6 millijoules (50% of 5.8 mJ). In one example, processor 34 may be configured to determine that a pump stroke is from an empty reservoir 30 when the energy required to recharge capacitor 88 is within between about 0.1 millijoules and about 2 millijoules of an expected recharge energy of a pump stroke from an empty reservoir, such as the 3.5 millijoules calculated above for the example of FIG. 9. In another example, processor 34 may be configured to determine that a pump stroke is from an empty reservoir when the recharge energy for capacitor 30 is within between about 5% and about 50% of the expected recharge energy for an empty pump stroke (e.g., for an expected recharge energy of 3.5 millijoules, between about 0.17 millijoules 5% of 3.5 mJ) and about 1.8 millijoules (~50% of 3.5 mJ).

In one example, rather than analyzing individual pump strokes, processor 34 may be configured to determine that reservoir 30 is empty when the energy required to recharge capacitor 88 from a predetermined percentage of the plurality of pump strokes indicate that reservoir 30 is empty, such as when at least about 50%, at least about 60%, at least about 75%, at least about 80%, or at least about 90%, or 100% of a plurality of recent pump strokes are within a predetermined threshold of an expected recharge energy for an empty-reservoir pump stroke. Processor 34 may also be configured to determine when a predetermined number of consecutive pump strokes require an amount of energy to recharge capacitor 88 that is within a predetermined threshold of the expected recharge energy after an empty-reservoir pump stroke, such as at least 5 consecutive pump strokes, at least 7 consecutive pump strokes, or at least 10 consecutive pump strokes. If fewer than the predetermined number or percentage of pump strokes are within the predetermined threshold of the expected recharge energy for an empty-reservoir pump stroke, then processor 34 may determine that reservoir 30 is not empty, e.g., that reservoir 30 contains some therapeutic agent.

The capacitor recharge energy and the variance from the recharge energy may depend on characteristics of the fluid being delivered, such as the molecular weight of a drug being delivered or a viscosity of the therapeutic agent fluid. Therefore, the expected recharge energy for capacitor 88 for a normal pump stroke or an empty-reservoir pump stroke may be altered depending on the fluid being delivered. Another factor that may affect the expected recharge energy is the battery depletion over the life of IMD 12.

In addition to using the energy needed to drive actuator 52 to determine if reservoir 30 is empty, other methods may be used to detect an empty reservoir 30. For example, as illustrated in FIGS. 3 and 4, IMD 12 may include sensor 166 that detects a change in noise made by actuator 52. As actuator 52 moves through the pump stroke, a portion of actuator 52 may strike another portion of IMD 12, which produces noise that is detectable by sensor 166. In one example, a noise is generated when armature 72 of actuator 52 strikes magnetic cup 66 at the end of a pump stroke, which will generally be referred to in the disclosed examples herein as a "stop noise." The character of the stop noise is different when reservoir 30 contains the therapeutic agent compared to when reservoir 30 is empty such that actuator 52 makes a first noise at an end of a normal pump stroke when the therapeutic agent is in reservoir 30 and actuator 52 makes a second noise at the end of the pump stroke when reservoir 30 is empty. For example, the first noise after a normal pump stroke may be a different type of sound than the second noise, including, e.g. a "thud" rather than a "ping." The type of noise may be characterized by auditory factors including sound amplitude, sound frequency, and sound duration. In such examples, sound sensor 166 may be configured to detect and to discriminate between the first type of stop noise (e.g. thud) and the second type of stop noise (e.g. ping) to determine if the noise is a type associated with a pump stroke from an empty reservoir 30. In another example, the volume, e.g., the loudness, of the first noise may be different from the volume of the second noise, such as the second noise being louder, and sensor 166 may be configured to detect a different noise volume associated with a pump stroke from an empty reservoir 30.

In one example, the character of the stop noise may depend on characteristics of the fluid being delivered, such as the molecular weight of a drug being delivered or a viscosity of the therapeutic agent fluid. Therefore, the expected starting voltage across capacitor 88 for a normal pump stroke or an empty-reservoir pump stroke may be altered depending on the fluid being delivered. Another factor that may affect the expected starting voltage is the battery depletion over the life of IMD 12.

Sensor 166 may be a sound sensor that can detect the actual, audible noise that is made by actuator 52, i.e. the stop noise, or it may be a vibration sensor that can detect vibrations within IMD 12 associated with a stop noise of actuator 52 and determine if the stop noise is associated with a pump stroke from an empty reservoir 30. In the example shown in FIG. 3, sound sensor 166 is provided proximate actuator 52 such that the sound of the first noise or the second noise passes through pump 40 to sound sensor 166. Also in the example shown in FIG. 3, sound sensor 166 is located proximate magnetic cup 66 so that when armature 72, strikes magnetic cup 66, the stop noise is transmitted through magnetic cup 66 where it is picked up by sound sensor 166.

In one example, sound sensor 166 comprises a piezoelectric device that produces a voltage in response to stresses on the piezoelectric material associated with the stop noise. The differences between a first stop noise associated with a normal pump stroke and a second stop noise associated with an empty reservoir can be detected by analyzing the voltage output from the piezoelectric material. For example, if the difference between the first stop noise and the second stop noise is the volume of the noise produced, the resulting voltage produced by the piezoelectric material may be expected to be higher for the second stop noise because it would result in a greater warping of the piezoelectric material. If the first stop noise and the second stop noise are different types of sounds, then the shape of the voltage waveform produced by the piezoelectric material may be different for the first and second stop noises. Examples of piezoelectric materials that may be used in sound sensor 166 include piezoelectric ceramics, such as lead zirconate titanate (PZT), piezoelectric crystals, such as gallium phosphate, quartz, or tourmaline, and piezoelectric polymers, such as polyvinylidene fluoride (PVDF).

In one example, IMD 12 may include a piezoelectric alarm component that is configured to produce an audible alarm sound when a voltage is applied to a piezoelectric material by an alarm drive circuit. In one example, processor 34 of IMD 12 causes the alarm drive circuit to apply a voltage to the piezoelectric material of the piezoelectric alarm component in order to produce the alarm noise in various situations in order to alert a patient, such as when an error within IMD 12 requires a decision by the patient or a clinician treating the patient. The piezoelectric alarm component can also be configured to act as sound sensor 166 by also connecting the piezoelectric material to a sensor circuit that will detect the voltage output by the piezoelectric material that is associated with the stop noise. In one example, the alarm drive circuit that applies a voltage to piezoelectric alarm/sound sensor 166 is shut off during normal operation of IMD 12 and is only turned on when an alarm condition is detected, while the sensor circuit that analyzes the voltage output of piezoelectric sound sensor 166 is on during normal operation of IMD 12 but is shut off when the alarm condition is detected.

Sensors other than a sound sensor may be used to detect and discriminate between the first stop noise created during a normal pump stroke when reservoir 30 contains the therapeutic agent and the second stop nose created from a pump stroke when reservoir 30 is empty of the therapeutic agent. In one example, a vibration sensor may be used that detects vibrations that pass through IMD 12 as a result of the stop noise of actuator 52. A vibration sensor is similar to the sound sensor 166 described above, but a vibration sensor may be configured to detect vibrations in IMD 12 that may not rise to the level of an audible sound. In this way, a vibration sensor may be located anywhere in IMD 12 such that the sensor may detect vibrations associated with the stop noise of actuator 52, whereas a sound sensor may require placement proximate actuator 52 to ensure detection of the actual, audible stop noise produced. An example of a vibration sensor that may be used to detect and discriminate between the first stop noise and the second stop noise is an accelerometer.

In one example, a sensor that is used for another purpose may also be configured to act as a vibration sensor that detects the change between the first stop noise and the second stop noise. For example, as already described above, a piezoelectric alarm component can also be configured to act as a piezoelectric sound sensor. In another example, a machine health monitor may be employed within IMD 12 to detect mechanical faults within medical pump 40. The machine health monitor may also be configured to detect vibrations associated with the stop noise and to determine whether the vibrations correspond to a first stop noise or a second stop noise. In another example, a posture sensor, e.g. an accelerometer used to detect the posture of a patient and deliver adaptive therapy based thereon may also be used to detect vibrations associated with the stop noise and to determine whether the vibrations correspond to a first stop noise or a second stop noise.

In one example, rather than processor 34 using individual stop noises or vibrations detected by sensor 166 to determine if reservoir 30 is empty, processor 34 may be configured to determine that reservoir 30 is empty when the stop noise or vibration from a predetermined percentage of a plurality of pump strokes indicate that reservoir 30 is empty, such as when at least about 50%, at least about 60%, at least about 75%, at least about 80%, or at least about 90%, or 100% of a plurality of recent pump strokes produces a noise or vibration that corresponds to an empty-reservoir pump stroke. Processor 34 may also be configured to determine when a predetermined number of consecutive pump strokes produce a noise or vibration that corresponds to an empty-reservoir pump stroke, such as at least 5 consecutive pump strokes, at least 7 consecutive pump strokes, or at least 10 consecutive pump strokes. If fewer than the predetermined number or percentage of pump strokes produce a noise or vibration that corresponds to an empty-reservoir pump stroke, then processor 34 may determine that reservoir 30 is not empty, e.g., that reservoir 30 contains some therapeutic agent.

As will be apparent to a person of ordinary skill in the art, although the block diagram of FIG. 4 shows coil current sensor 100, coil voltage sensor 102, and capacitor coil sensor 104, which may be used to determine the energy of each pump stroke, and sound sensor 166 to analyze a stop noise produced by actuator 52 as all being included as part of IMD 12, the present disclosure is not so limited. An IMD could include only one of sensors 100, 102, 104, and 166 to provide for the determination that reservoir 30 is empty. Similarly, an IMD could include any combination of sensors 100, 102, 104, and 166 in order to provide redundancy in the determination that reservoir 30 is empty. Additionally, a separate implanted or external device including one or more of sensors 100, 102, 104, and 166 may be communicatively connected to and employed in conjunction with an IMD to treat a patient.

Figure 10:
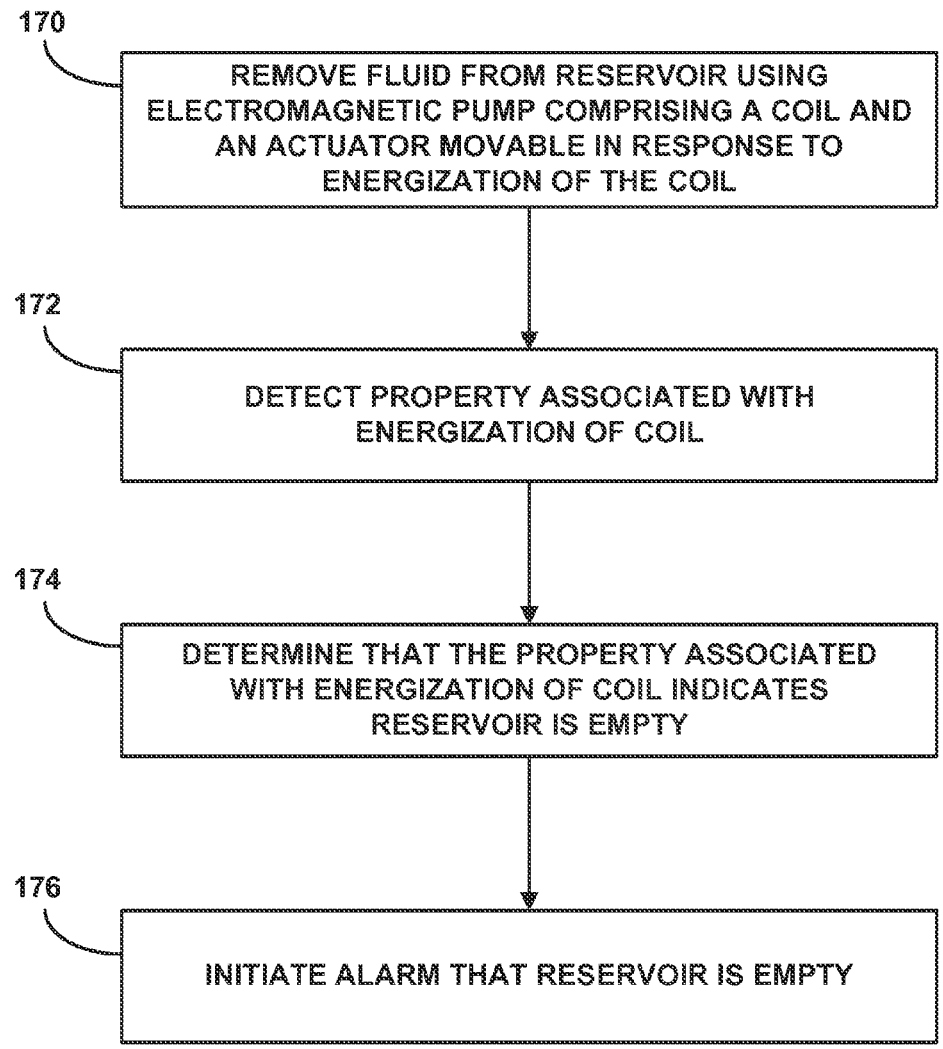
FIG. 10 is an example method for determining that a medical pump reservoir is empty.

FIG. 10 shows a flowchart of an example method of determining if reservoir 30 is empty or near empty. The example method includes removing fluid from reservoir 30 using an electromagnetic pump 40 (170), wherein pump 40 comprises an actuation mechanism configured to be energized to provide a pump stroke, such as a coil 50 and an actuator 52 that is movable in response to the energization of coil 50. Next, a property associated with the energization of coil 50 is detected (172). Finally, it is determined that the property associated with the energization of coil 50 indicates that reservoir 30 is empty (174). As described above, the property associated with the energization of coil 50 may comprise one of several methods. In one example, the property associated with the energization of coil 50 comprises the shape of a current waveform through coil 50 when providing for a pump stroke when "reservoir 30 is empty. In another example, the property associated with the energization of coil 50 comprises a total energy supplied to coil 50 in order to produce the pump stroke when reservoir 30 is empty, such as through the use of Equation 1 or Equation 2. In another example, the property associated with the energization of coil 50 comprises a voltage across coil 50 after the completion of a pump stroke when reservoir 30 is empty. In another example, the property associated with the energization of coil 50 comprises a total energy supplied by power source 42 to coil 50 in order to produce the pump stroke when reservoir 30 is empty. In another example, the property associated with the energization of coil 50 comprises a time to recharge capacitor 88 after a selective energization of coil 50 by capacitor 88 in order to produce the pump stroke when reservoir 30 is empty. In another example, the property associated with the energization of coil 50 comprises the energy required to recharge capacitor 88 after a selective energization of coil 50 by capacitor 88 in order to produce the pump stroke when reservoir 30 is empty, such as through the use of Equation 3. In yet another example, the property associated with the energization of coil 50 comprises a voltage across capacitor 88 after the completion of a pump stroke when reservoir 30 is empty.

Detecting the property associated with the energy required to energy the actuation mechanism (172) may be performed by a sensor, such as sensor 100, 102, or 104 described above, which may provide an output. Determining if the property associated with the energy required to energize the actuation mechanism indicates reservoir 30 is empty (174) may be performed by a processor that analyzes the output from the sensor. In one example, processor 34 of IMD 12 may analyze the output of the sensor and determine if the property associated with the energy required to energize the actuation mechanism indicates reservoir 30 is empty. In another example, a processor of another computing device, such as a processor of external programmer 20, may determine if the property associated with the energy required to energize the actuation mechanism indicates reservoir 30 is empty.

As described in more detail elsewhere in this disclosure, an indication that reservoir 30 is empty may include determining that the property associated with energization of coil 50 is within a certain threshold of a value or characteristic of the property associated with energization of coil 50 that is expected when reservoir 30 is empty or near empty. Other methods may be used to indicate that reservoir 30 is empty or near empty, including anything with respect to the property associated with energization of coil 50 that is connected to, related to, demonstrates, suggests, signifies, specifies, or is a sign that reservoir 30 is empty or near empty.

The method of FIG. 10 may also include initiating an alarm (176) when it is determined that the property associated with the energization of coil 50 indicates the reservoir is empty or near empty. In one example, initiating the alarm may comprise activating the alarm drive circuit of piezoelectric sensor/alarm 166 in order to produce an audible alarm. The alarm may also comprise a vibrational alarm that is felt by the patient, or a signal sent by IMD 12 to another device, such as an external computing device, for example programmer 20, in order to draw a user's attention, such as an audible, visual, textual, or other type of alert that is perceived by a user, such as the patient or a clinician.

Several methods have been described to determine when reservoir 30 is "empty." However, the methods described above for detecting when reservoir 30 is completely empty may be used to determine when reservoir 30 is nearly empty. For example, as described above, the shape of the current waveform through coil 50 is different when reservoir contains some therapeutic agent as compared to an empty reservoir, as is apparent by the difference between waveform 110 and 112 in FIG. 5. However, the waveform shape does not change from that of waveform 110 (normal pump stroke) to that of waveform 112 (empty reservoir) instantaneously. Rather, when reservoir 30 reaches a certain level, the current waveform starts to gradually change until it eventually settles as the empty-reservoir waveform 112. During this transition, the actual waveform for a particular pump stroke may be somewhere between waveform 110 and waveform 112. However, processor 34 may be configured to determine when the current waveform approximates one of the waveforms during this transition so that IMD 12 may determine when reservoir 30 is "near empty" rather than having to wait until reservoir 30 is completely empty. This transition may start when reservoir 30 is "near empty," e.g., when reservoir 30 is about 5 percent full.

The voltage across coil 50 may also gradually change from voltage waveform 150 to voltage form 152, and any of the waveforms in the transition between voltage waveform 150 and voltage waveform 152 may be used to determine that reservoir is nearly empty. For example, processor 34 may be configured so that when the calculation of Equation 1 results in a calculated energy that is somewhere between that calculated from normal voltage waveform 150 and empty-reservoir voltage waveform 152 may trigger processor 34 to determine that reservoir 30 is "near empty." Similarly, the voltage across capacitor 88 as it is recharged may change gradually from recharge curve 160 for a normal pump stroke to recharge curve 162 for a pump stroke from a completely empty reservoir 30. Processor 34 may be configured to determine when a recharge curve somewhere between recharge curve 160 and recharge curve 162 occurs to determine that reservoir 30 is near empty. Therefore, anytime a method is described above as being for determining when reservoir 30 is "empty," the same method may be used to determine when reservoir 30 is "near empty" without varying from the scope of the present disclosure.

In one example, processor 34 may be configured to detect both a nearly empty reservoir 30 and a completely empty reservoir 30 and to initiate different alarms for each. When reservoir 30 is nearly empty, processor initiates a first alarm, and when reservoir 30 becomes completely empty, processor initiates a second alarm. The first alarm, or near-empty alarm, and the second alarm, or empty alarm, may have difference characteristics, such as different audio qualities or a different intensity. The near-empty alarm and empty alarm may also comprise different types of alarms, such as near-empty alarm comprising a single audio alarm from IMD 12 or an external programmer 20 used by the patient, and the empty alarm comprising a repeating audio alarm and a visual alarm on the external programmer 20. In another example, the near-empty alarm may comprise an alarm that must be acknowledged by the patient, such as an audible and visual alarm that must be cleared by the patient, and an informational notice to a clinician, while the empty alarm may require acknowledgement by the clinician, such as a visual alarm that is displayed on an external computing device monitored by the clinician.

Figure 11:
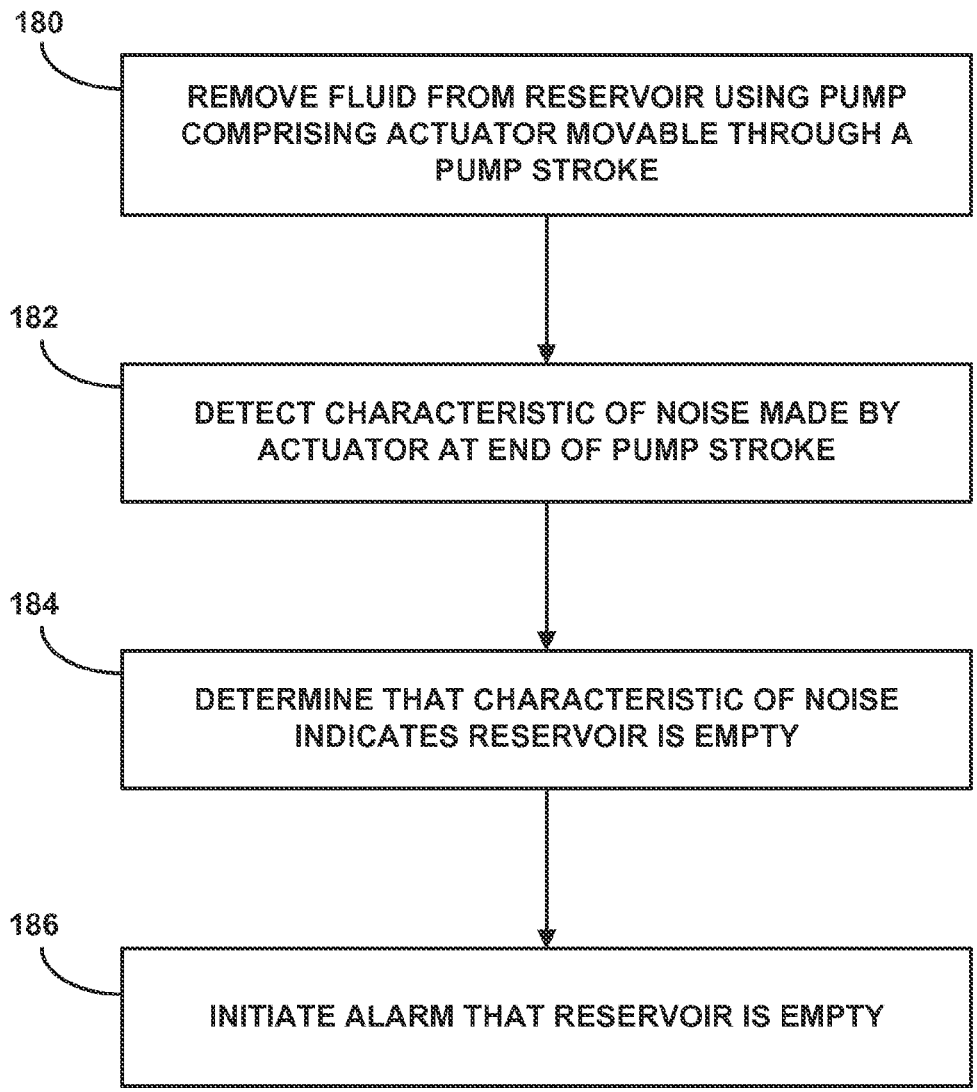
FIG. 11 is another example method for determining that a medical pump reservoir is empty.

FIG. 11 shows a flowchart of an example method of determining if reservoir 30 is empty. The example method includes removing fluid from reservoir 30 using pump 40 (180), wherein pump 40 comprises an actuator 52 that is movable through a pump stroke. Next, a characteristic of the noise made by actuator 52 at the end of a pump stroke is detected (182). Then, it is determined if the characteristic of the noise made by actuator 52 indicates reservoir 30 is empty (184). As described above, the characteristic of the noise may be the type of noise or the volume of the noise. The method may also include initiating an alarm when it is determined that reservoir 30 is empty (186).

As described in more detail elsewhere in this disclosure, an indication that reservoir 30 is empty may include determining that the characteristic of the noise made by actuator 52 is within a certain threshold of a value or characteristic of the characteristic of the stop noise that is expected when reservoir 30 is empty or near empty. Other methods may be used to indicate that reservoir 30 is empty or near empty, including anything with respect to the characteristic of the stop noise that is connected to, related to, demonstrates, suggests, signifies, specifies, or is a sign that reservoir 30 is empty or near empty.

Although the target therapy delivery site described with reference to the foregoing examples is proximate to the spinal cord of a patient, other applications of therapy systems in accordance with this disclosure include alternative delivery sites. In some examples, the target delivery site may be proximate to different types of tissues including, e.g., nerves, e.g. sacral, pudendal or perineal nerves, organs, muscles or muscle groups. In one example, a catheter may be positioned to deliver a therapeutic fluid to a deep brain site or within the heart or blood vessels.

Delivery of a therapeutic fluid within the brain may help manage a number of disorders or diseases including, e.g., chronic pain, diabetes, depression or other mood disorders, dementia, obsessive-compulsive disorder, migraines, obesity, and movement disorders, such as Parkinson's disease, spasticity, and epilepsy. A catheter may also be positioned to deliver insulin to a patient with diabetes. In other examples, the system may deliver a therapeutic fluid to various sites within a patient to facilitate other therapies and to manage other conditions including peripheral neuropathy or post-operative pain mitigation, ilioinguinal nerve therapy, intercostal nerve therapy, gastric drug induced stimulation for the treatment of gastric motility disorders and/or obesity, and muscle stimulation, or for mitigation of peripheral and localized pain e.g., leg pain or back pain.

The techniques described in this disclosure, including those attributed to processor 34 of IMD 12 and external programmer 20 may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

This disclosure refers to illustrative examples that are not meant to be construed in a limiting sense. Various modifications of the illustrative examples, as well as additional examples of the disclosure, will be apparent to persons skilled in the art upon reference to this description. Any specific numerical value or range described in the foregoing disclosure shall not be limiting, except for values or ranges included in the following claims.

The invention claimed is:

1. A medical device system comprising:
   a reservoir configured to store a therapeutic fluid;
   a medical pump configured to receive at least a portion of the therapeutic fluid from the reservoir and deliver the portion of the therapeutic fluid to a patient, the pump comprising an actuator that is movable through a pump stroke, wherein the actuator makes a noise associated with the pump stroke at an end of the pump stroke;
   a sensor configured to detect a characteristic of the noise; and
   a processor configured to determine that the characteristic of the noise indicates the reservoir is empty or near empty, wherein the characteristic of the noise comprises at least one of an amplitude of the noise, a frequency of the noise, and a duration of the noise.

2. The system of claim 1, wherein to determine that the characteristic of the noise indicates the reservoir is empty or near empty, the processor is configured to determine a difference between the characteristic of the noise and the characteristic of a noise associated with each of one or more previous pump strokes.

3. The system of claim 1, wherein to determine that the characteristic of the noise indicates the reservoir is empty or near empty, the processor is configured to determine a difference between the characteristic of the noise and the characteristic of a noise that is expected when the reservoir is empty or near empty.

4. The system of claim 1, wherein to determine that the characteristic of the noise indicates the reservoir is empty or near empty, the processor is configured to determine one of:
   that the characteristic of a noise associated with each of a predetermined number of a set of pump strokes indicates the reservoir is empty or near empty, wherein the predetermined number of the set of pump strokes includes the pump stroke; or
   that the characteristic of a noise associated with each of a predetermined number of consecutive pump strokes indicates the reservoir is empty or near empty, wherein the predetermined number of the consecutive pump strokes includes the pump stroke.

5. The system of claim 1, wherein the sensor comprises a piezoelectric material configured to detect vibrations associated with the noise, and wherein the characteristic of the noise comprises a characteristic of the vibrations associated with the noise.

6. The system of claim 1, wherein the sensor comprises a machine health monitor configured to detect mechanical faults within the pump, the machine health monitor being further configured to detect vibrations associated with the noise, and wherein the characteristic of the noise comprises a characteristic of the vibrations associated with the noise.

7. The system of claim 1, wherein the sensor comprises a posture sensor configured to detect a posture of the patient, the posture sensor being further configured to detect vibrations associated with the noise, and wherein the characteristic of the noise comprises a characteristic of the vibrations associated with the noise.

8. The system of claim 1, wherein the processor is further configured to initiate an alarm upon determining that the characteristic of the noise indicates the reservoir is empty or near empty.

9. The system of claim 1, wherein an implantable device comprises the reservoir and the medical pump.

10. A medical device system comprising:
    means for storing a therapeutic fluid;
    means for delivering at least a portion the therapeutic fluid received from the means for storing the therapeutic fluid, the means for delivering the therapeutic fluid comprising means for actuating the fluid and to provide a pump stroke, wherein the means for actuating the fluid makes a noise associated with the pump stroke at an end of the pump stroke;
    means for detecting a characteristic of the noise; and
    means for determining that the characteristic of the noise indicates the means for storing the therapeutic fluid is empty or near empty, wherein the characteristic of the noise comprises at least one of an amplitude of the noise, a frequency of the noise, and a duration of the noise.

11. The system of claim 10, wherein the means for determining that the characteristic of the noise indicates the reservoir is empty or near empty comprises means for determining a difference between the characteristic of the noise and the characteristic of a noise associated with each of one or more previous pump strokes.

12. The system of claim 10, wherein the means for determining that the characteristic of the noise indicates the reservoir is empty or near empty comprises means for determining a difference between the characteristic of the noise and the characteristic of a noise that is expected when the reservoir is empty or near empty.

13. The system of claim 10, wherein the means for determining that the characteristic of the noise indicates the reservoir is empty or near empty comprises means for determining one of:
    that the characteristic of a noise associated with each of a predetermined number of a set of pump strokes indicates the reservoir is empty or near empty, wherein the predetermined number of the set of pump strokes includes the pump stroke; or
    that the characteristic of a noise associated with each of a predetermined number of consecutive pump strokes indicates the reservoir is empty or near empty, wherein the predetermined number of the consecutive pump strokes includes the pump stroke.

14. The system of claim 10, wherein the means for detecting the characteristic of the noise comprises a piezoelectric material configured to detect the vibrations associated with the noise, and wherein the characteristic of the noise comprises a characteristic of the vibrations associated with the noise.

15. The system of claim 10, wherein the means for detecting the characteristic of the noise comprises a machine health monitor configured to detect mechanical faults within the pump, the machine health monitor being further configured to detect the vibrations associated with the noise, and wherein the characteristic of the noise comprises a characteristic of the vibrations associated with the noise.

16. The system of claim 10, wherein the means for detecting the characteristic of the noise comprises a posture sensor configured to detect a posture of the patient, the posture sensor being further configured to detect the vibrations associated with the noise, and wherein the characteristic of the noise comprises a characteristic of the vibrations associated with the noise.

17. The system of claim 10 further comprising means for initiating an alarm upon determining that the characteristic of the noise indicates the reservoir is empty or near empty.

18. The system of claim 10, wherein an implantable device comprises the means for storing the therapeutic fluid and the means for removing the therapeutic fluid.

19. A method comprising:
- delivering, by a medical pump of a medical device, at least a portion of therapeutic fluid received from a reservoir of the medical device, the medical pump comprising an actuator that is movable through a pump stroke, wherein the actuator makes a noise associated with the pump stroke at an end of the pump stroke;
- detecting, by a sensor, a characteristic of the noise; and
- determining, by a processor, that the characteristic of the noise indicates the reservoir is empty or near empty, wherein the characteristic of the noise comprises at least one of an amplitude of the noise, a frequency of the noise, and a duration of the noise.

20. The system of claim 19, wherein determining that the characteristic of the noise indicates the reservoir is empty or near empty comprises determining a difference between the characteristic of the noise and the characteristic of a noise associated with each of one or more previous pump strokes.

* * * * *